(12) United States Patent
Fliri

(10) Patent No.: US 11,120,346 B2
(45) Date of Patent: Sep. 14, 2021

(54) METHOD AND DESCRIPTORS FOR COMPARING OBJECT-INDUCED INFORMATION FLOWS IN A PLURALITY OF INTERACTION NETWORKS

(71) Applicant: Anton Franz Joseph Fliri, Stonington, CT (US)

(72) Inventor: Anton Franz Joseph Fliri, Stonington, CT (US)

(73) Assignee: SystaMedic Inc., Stonington, CT (US)

( * ) Notice: Subject to any disclaimer, the term of this patent is extended or adjusted under 35 U.S.C. 154(b) by 773 days.

(21) Appl. No.: 15/778,448

(22) PCT Filed: Nov. 25, 2016

(86) PCT No.: PCT/US2016/063792
§ 371 (c)(1),
(2) Date: May 23, 2018

(87) PCT Pub. No.: WO2017/091822
PCT Pub. Date: Jun. 1, 2017

(65) Prior Publication Data
US 2018/0349779 A1 Dec. 6, 2018

Related U.S. Application Data

(60) Provisional application No. 62/260,088, filed on Nov. 25, 2015.

(51) Int. Cl.
*G06N 5/04* (2006.01)
*G06F 16/28* (2019.01)
(Continued)

(52) U.S. Cl.
CPC ............ *G06N 5/04* (2013.01); *G06F 16/284* (2019.01); *G06N 3/12* (2013.01); *G16H 70/40* (2018.01);
(Continued)

(58) Field of Classification Search
None
See application file for complete search history.

(56) References Cited

U.S. PATENT DOCUMENTS 7,003,559 B1 2/2006 Nataraian et al.
8,880,521 B2 11/2014 Markus et al.
(Continued)

FOREIGN PATENT DOCUMENTS

EP 1556819 A2 7/2005

OTHER PUBLICATIONS

Villaverde, et al., MIDER: Network Inference with Mutual Information Distance and Entropy Reduction, PLoS ONE 9(5), 2014, pp. 1-15 (Year: 2014).*

(Continued)

*Primary Examiner* — Wilbert L Starks
(74) *Attorney, Agent, or Firm* — Ziegler IP Law Group, LLC

(57) ABSTRACT

A method of tracking information flows through multiple network systems includes selecting a primary network system from a population of primary and secondary network systems, wherein each of the primary and secondary network systems include network nodes, selecting first selected characteristic features that identify network nodes of the primary network system that provide interaction between the selected primary network system and secondary network systems, identifying at least one secondary network system that is capable of interacting with the network nodes of the primary network system, subdividing the primary network into subnetwork systems based on identifying primary network nodes that provide interaction between the primary network system and secondary network nodes, identifying the subnetwork systems that are capable of interacting with one or more network nodes of the secondary network
(Continued)

systems, identifying a subnetwork node count of the primary network nodes in each subnetwork, identifying objects that are capable of interacting with the primary network nodes, and determining a coincidence frequency or a coincidence measurement between features of objects interacting with the primary network nodes and the features of the primary network nodes that indicate information exchanges between the primary and secondary network nodes.

31 Claims, 5 Drawing Sheets

(51) Int. Cl.
H04L 12/24 (2006.01)
G16H 70/60 (2018.01)
G16H 70/40 (2018.01)
G06N 3/12 (2006.01)

(52) U.S. Cl.
CPC ............ *G16H 70/60* (2018.01); *H04L 41/12* (2013.01); *Y04S 40/00* (2013.01)

(56) References Cited

U.S. PATENT DOCUMENTS

| | | | |
|---|---|---|---|
| 8,976,710 | B2 | 3/2015 | Indukuri et al. |
| 2007/0168533 | A1 | 7/2007 | Canright et al. |
| 2014/0040264 | A1 | 2/2014 | Varadan et al. |
| 2014/0207945 | A1 | 7/2014 | Galloway et al. |
| 2014/0337820 | A1 | 11/2014 | Km |
| 2015/0081323 | A1 | 3/2015 | Jackson et al. |

OTHER PUBLICATIONS

Addanki, Online Sequential Extreme Learning Machines: Features Combined From Hundreds of Midlayers, arXiv:2006.06893, 2020, pp. 1-5 (Year: 2020).*

Burak Yoldemir et al. Stable Overlapping Replicator Dynamics for Brain Community Detection. IEEE Transactions on Medical Imaging, Sep. 2015.

Albert-Laszlo Barabasi et al. Network Biology: Understanding the Cell's Functional Organization. Nature Reviews Genetics Mar. 2004; 5(2):101-13.

Anton F Fliri, William T Loging, Robert A Volkmann. Analysis of information flows in interaction networks: implication for drug discovery and pharmacological research. Discovery medicine Feb. 2011; 11(57):133-43.

Lin et al. "The Application of Structural Holes Theory to Supply Chain Network Information Flow Analysis." [online] Information Technology Journal 10.1, published 2011, retrieved on Feb. 8, 2017 from https://www.researchgate.net/profile/Chun_Nan_Lin/publication/49941924_The_Application_of_Structural_Holes_Theory_to_Supply_Chain_Network_Information_Flow_Analysis/links/5549d18a0cf205bce7ac40a7.pdf, 6 pages.

International Search Report, Application No. PCT/US2016/063792, dated Mar. 2, 2017, 8 pages.

Cui, X., He, H., He, F. et al. Network fingerprint: a knowledge-based characterization of biomedical networks. Sci Rep 5, 13286 (2015) doi:10.1038/srep13286.

Ahn, Y., Bagrow, J. & Lehmann, S. Link communities reveal multiscale complexity in networks. Nature 466, 761-764 (2010) doi:10.1038/nature09182.

Extended European Search Report, Application No. 16869345.5 dated Mar. 29, 2019.

* cited by examiner

GENERAL METHOD FOR CONSTRUCTING DESCRIPTORS OF THE INVENTION

METHOD AND DESCRIPTORS FOR COMPARING OBJECT-INDUCED INFORMATION FLOWS IN A PLURALITY OF INTERACTION NETWORKS

This application claims the benefit of U.S. Provisional Application Ser. No. 62/260,088, filed on 25 Nov. 2015, incorporated by reference herein in its entirety.

The disclosed embodiments relate generally to information tracking, and more particularly to identifying information flows in multiple interacting dynamic network systems.

BACKGROUND

In the existing literature, the terms "information flow" and "information flow analysis" are usually used in reference to the analysis of computer network systems. Thus, a hall mark of computer network systems is that the information flowing through these network systems causes changes to the connectivity or network topology of these network systems. The term connectivity refers to the transfer of information from one network node to another and the term network node refers to a connection point or redistribution point for the propagation of information.

For example, network nodes transmit signals by affecting, directly or indirectly, properties of a set of neighboring network nodes which, in turn, affect properties of neighboring nodes of the set of neighboring nodes, and in turn propagate changes to all network nodes involved in the distribution of the signals, which may include network nodes throughout a plurality of connected network systems. The propagation of the signals through these network systems depends on attributes of the signals and the topology of the network systems. A network system's ability to vary network topologies as a consequence of the signals flowing through the network system enables the injection of a plurality of simultaneous signals for formulating the network system's response to input signals.

While the computer industry has developed many tools for information flow analysis and implementation, this is not the case for analysis of biological or social network systems.

SUMMARY

Analyzing the complexity of a regulatory scheme of biological or social network systems requires special tools and methods for determining relationships between network topologies, the routing of information flows through a plurality of interacting dynamic network systems, and the qualities of objects or persons interacting with these dynamic network systems. Understanding how these interacting relationships affect regulatory functions of complex network systems is at least one key for predicting behavior of organisms and responses of complex systems to network perturbations.

In the existing literature, the terms "information flow" and "information flow analysis" are usually used in reference to the analysis of computer programs that combine elements of control flow and data flow analysis in some manner. However, in this application these terms are used to describe the utility of novel descriptors and methods that determine the distribution of information associated with objects or persons in dynamic interaction networks, social networks and biological networks and use this information for predicting, describing and managing the behavior of objects, or persons that exchange information with these network systems.

The presently disclosed embodiments are directed to a method for creating new descriptor sets for biological substances, man-made devises or persons that allow the tracking of information flows caused by "objects/persons" in multiple interacting dynamic network systems. These new descriptor sets are anticipated to be useful for the diagnosis of disease, for interpreting the significance of changes in physiologic measurements produced by devices used for monitoring physiologic parameters, for predicting effects of biologically active substances in biological systems, for determining the spread of infectious agents in social networks, for selecting and managing portfolios consisting of biological active agents, financial instruments, products and for evaluating behaviors of persons exchanging information via social networks or dynamic interaction networks. However, although the applications of the described methodology and descriptors are myriad, a focus of this patent application is to describe the manufacture of descriptors of objects or persons enabling the tracking of information flows in biological or social networks systems.

For purposes of the disclosed embodiments, the term object may include, without limitation, one or more of contagions, man-made or natural occurring biologically active substances and mixtures thereof, medicines of various origins, plants, microorganisms, devices that measure functions of biological systems, and persons interacting with social network systems.

The disclosed embodiments are directed to a method of tracking information flows through multiple network systems including selecting a primary network system from a population of primary and secondary network systems, wherein each of the primary and secondary network systems comprise network nodes, selecting first selected characteristic features that identify network nodes of the primary network system that provide interaction between the selected primary network system and secondary network systems, identifying at least one secondary network system that is capable of interacting with the network nodes of the primary network system, subdividing the primary network into subnetwork systems based on identifying primary network nodes that provide interaction between the primary network system and secondary network nodes, identifying the subnetwork systems that are capable of interacting with one or more network nodes of the secondary network systems, identifying a subnetwork node count of the primary network nodes in each subnetwork, identifying objects that are capable of interacting with the primary network nodes, and determining a coincidence frequency or a coincidence measurement between features of objects interacting with the primary network nodes and the features of the primary network nodes that indicate information exchanges between the primary and secondary network nodes.

The first selected characteristic features may be selected from proper names, synonyms or symbols of network nodes of interaction network systems, measurements associated with network nodes of interaction network systems, a plurality of measurements associated with network nodes of interaction network systems, proper names and synonyms of groups of network nodes of interaction networks, symbols of network nodes of interaction network systems, and symbols of groups of network nodes of interaction network systems.

Identifying at least one secondary network system that is capable of interacting with the network nodes of the primary network system may include randomly selecting second selected characteristic features of network nodes of randomly selected interaction networks stored in a database, using the first selected characteristic features and the second selected characteristic features for determining coincidence frequencies or coincident measurements of the first selected characteristic features with the second selected characteristic features and recording the results, and using the recorded coincidence frequency or coincidence measurement results for selecting one or more secondary network systems having at least one network node capable of interacting with the primary network system.

The database may include one or more of the Medline database, PubMed databases, EMBL databases, World Traditional Medicine Patent Database, Chinese Traditional Medicine Database, complementary and alternative medicine databases, Wikipedia, collections of digitized publications, measurements collected by surveillance systems, measurements collected by bio-surveillance systems, measurements collected by diagnostic systems, measurements collected by wearable devices, measurements collected by wearable electronic systems, measurements collected by wearable sensors, measurements collected by wearable diagnostic systems, measurements collected through crowd sourcing, medical record databases, adverse event reporting system databases, DHARA databases, and Ayurveda health care system databases.

The secondary network systems may include one or more of the internet, social networks, ecologic networks, biologic networks, nutrient networks, biologic communication networks, epidemiologic networks, protein networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks, military networks, immunologic networks, and intelligence networks.

Subdividing the primary network into subnetworks may include selecting characteristic features of the primary network nodes, selecting characteristic features of the secondary network nodes, and using the characteristic features of the primary network nodes and secondary network nodes for determining coincident measurements or co-occurrence frequency measurements indicating interactions between the primary network nodes and secondary network nodes in the database and recording the results.

The method may include determining the capacity of the objects to affect information transfer between the primary network system and a selected secondary network system using a first process including selecting ontologies of the subnetworks, and selecting ontologies of objects capable of interacting with said subnetwork for determining coincidence frequencies or coincidence measurements between instances in said subnetworks ontologies and instances in said object ontologies, and recording the result for said co-occurrence frequency or coincidence measurements, a second process including selecting a threshold for said co-occurrence frequency or coincidence measurements for determining the number of subnetwork nodes in subnetworks having co-occurrence frequencies or coincidence measurements above said selected threshold, and recording the results as object reachable subnetwork node counts of the subnetworks or as edge density measurements for said object and said subnetworks, and storing the results as edge density based object descriptors that provide estimates for the capacity of the objects to affect a transfer of information between the primary network system and a selected plurality of the secondary network systems.

The method may further include normalizing the edge density based object descriptors by determining ratios of the edge density measurements and the subnetwork node counts of the subnetworks of the primary network system.

The ratios may be determined using an instance of object associated edge density measurements as a numerator and an instance of subnetwork node counts of subnetworks of the primary network as a denominator, and the method includes recording the resulting node count ratios.

The ratios may be determined using an instance of object associated edge density measurements as a denominator and an instance of subnetwork node counts of subnetworks of the primary network as a numerator, and the method includes recording the resulting node count ratios.

The method may include aggregating the count ratios for the selected subnetworks and using the aggregated count ratios as estimates of the capacity of objects to affect information transfer between selected subnetworks of the selected primary network system and a selected secondary network system.

The method of may include determining a second set of descriptor sets by identifying objects that are capable of interacting with the primary network nodes by selecting characteristic features of the objects and determining occurrence frequencies or coincident measurements between the selected characteristic features of the objects and characteristic features of the primary network nodes, identifying and counting a number of network nodes in each subnetwork of the primary network that are capable of interacting or exchanging information with the identified objects, recording the node counts as focused subnetwork node counts, adding the co-occurrence frequency or coincident measurements of objects associated with respective subnetwork node of subnetworks of the primary network and recording the results as identifying a sum of co-occurrence frequency measurements for the objects obtained for each subnetworks node of subnetworks of the primary network, storing the sum of co-occurrence frequency measurements of said objects for said subnetwork node counts of the primary network as information density measurements of the objects, wherein the information density measurements of said objects provide estimates of the capacity of objects to affect information transfer between the subnetworks and the selected secondary network systems.

The method may include using the second descriptor set in hierarchical cluster analysis to identify groups of objects that induce similar routing of information flows in a plurality of interacting network systems and groups of network topologies regulating similar information flows.

The method of may include using the edge density based object descriptors for information flow analysis.

The method may include using the second descriptor set for information flow analysis.

The subnetwork ontologies may be derived from protein networks for creating the descriptors for information flow analysis The sub network ontologies may be disease based and derived from protein networks for creating the descriptors for information flow analysis The sub network ontologies may be MedDRA Term based sub network ontologies derived from protein networks for creating the descriptors for information flow analysis The sub network ontologies may be physiology based sub network ontologies derived from protein networks for creating the descriptors for information flow analysis The method may include using the second descriptor set for information flow analysis for selected herbs and drugs using disease based sub network ontologies derived from protein networks.

The method may include using the second descriptor set for information flow analysis for selected herbs and drugs using MedDRA Term based sub network ontologies derived from protein networks.

The method may include using the second descriptor set for information flow analysis for selected herbs and drugs using physiology based sub network ontologies derived from protein networks.

The method may include using the edge density based object descriptors for information flow analysis for selected herbs and drugs using disease based sub network ontologies derived from protein networks.

The method may include using the edge density based object descriptors for information flow analysis for selected herbs and drugs using MedDRA Term based sub network ontologies derived from protein networks.

The method may include using the edge density based object descriptors for information flow analysis for selected herbs and drugs using physiology based sub network ontologies derived from protein networks.

The disclosed embodiments are also directed to a method for producing novel descriptors of objects or persons including a first step of selecting a first set of characteristic features of network-nodes of a first interaction network system of interest further comprising the use of said selected characteristic features of said network nodes of said first selected interaction network system for creating a first descriptor set of said first interaction network system, wherein the characteristic features may be selected from the group comprising proper names, synonyms or symbols of network nodes of interaction network systems, measurements associated with network nodes of interaction network systems, a plurality of measurements associated with network nodes of interaction network systems, proper names and synonyms of groups of network nodes of interaction networks, symbols of network nodes of interaction network systems, symbols of groups of network nodes of interaction network systems, wherein the interaction network systems may be selected from the group comprising the internet, social networks, ecologic networks, biologic networks, epidemiologic networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks, a second step of using said first descriptor set of said first network system for selecting a second, third, fourth . . . nth interaction network system interacting directly or indirectly or exchanging information directly or indirectly with said first interaction network system by using a first process for randomly selecting characteristic features of network-nodes of randomly selected interaction networks in a databases, a second process using said first descriptor set of said first network system and said randomly selected characteristic features of network nodes of said randomly selected interaction network system for determining coincidence frequencies or coincident measurements of said first descriptor set with said randomly selected characteristic features of network nodes of said randomly selected interaction networks in said database and recording the results, and a third process using said recorded results for selecting a second, third, fourth . . . nth interaction network system possessing at least one network node capable of interacting with or exchanging information with said first selected interaction network system, wherein the database may be selected from the group comprising the Medline database, PubMed databases, EMBL databases, World Traditional Medicine Patent Database, Chinese Traditional Medicine Database, complementary and alternative medicine database, Wikipedia, collections of digitized publications, measurements collected by surveillance systems, measurements collected by bio surveillance systems, measurements collected by diagnostic systems, measurements collected by wearable devices, measurements collected by wearable electronic systems, measurements collected by wearable sensors, measurements collected by wearable diagnostic systems, measurements collected through crowd sourcing, medical record database, adverse event reporting system database, DHARA database, Ayurveda health care system databases, wherein the second process for determining coincidence frequencies or coincident measurements comprises the selection of an instance of a first descriptor set and the selection of an instance of a second descriptor set and the selection of a database and the use of a text mining means for determining how often an instance of a first descriptor set co-occurs with an instance of a second descriptor set in said database and recording the results; likewise determination of coincidence measurements comprises the selection of an instance of a first descriptor set and the selection of an instance of a second descriptor set and the selection of a data bases and the use of a means for identifying measurements relating an instance of a first descriptor set and an instance of a second descriptor set in said database and recording the results;

a third step comprising a third method for selecting a second, third, fourth . . . nth set of characteristic features of network-nodes of said second, third, fourth, nth interaction network system further comprising the use of said second, third, fourth . . . nth set of characteristic features of said network nodes of said second, third, fourth, . . . nth interaction network system for creating a second, third, fourth . . . nth descriptor set of said second, third, fourth . . . nth interaction network system selected in said second step.

a fourth step comprising a fourth method using said first descriptor set of said first interaction network system and using said second, third, fourth . . . nth descriptor set of said second, third, fourth . . . nth interaction network system and said second process of said second step and said databases for selecting subsets of descriptor sets of said first interaction network systems describing subsets of network nodes of said first interaction network system interacting directly or indirectly or exchanging information directly or indirectly with network nodes of said second, third, fourth . . . nth interaction network system.

a fourth process for determining the number of network nodes in said first, second, third, fourth subnetwork system of said first interaction network systems and recording the results wherein said results may be termed first, second, third, fourth . . . nth subnetwork-node counts of said subnetwork system of said first interaction network system are further termed SN1-nCN1 a fifth step comprising a fifth method for selecting a finite set of objects termed O1-m interacting directly or indirectly or exchanging information directly or indirectly with said first interaction network system, wherein said fifth method comprises a fifth process using said first descriptor set of said first interaction network system and using randomly selected characteristic features of randomly selected objects and said second process of said second step and said databases for determining coincidence frequencies or coincident measurements of said first descriptor set with said randomly selected characteristic features of said randomly selected objects in said databases.

selecting coincidence frequency measurements or a coincident measurement threshold and using said threshold for selecting incidences of said coincidence frequency measurements or said coincident measurements for said descriptor sets in said databases and recording the results.

using said selected coincidence frequency measurements or coincident measurements for selecting objects capable of interacting or exchanging information with at least one or a plurality of network nodes of said first selected interaction network system and recording said selected objects in a database.

wherein the objects are selected from the group comprising members of social networks, members of financial networks, members of ecologic networks, prescription medicines, over the counter drugs, medicinal herbs, natural products, Ayurvedic medicines, Chinese traditional medicines, Natural medicines, bacteria, algae, Organic and inorganic chemical compositions, Foods, nutrients, vitamins, microorganisms, viruses, supplements, vitamins, mobile devices, patients, clients, communities, members of communities, financial instruments, bonds, companies, members of physiologic networks, members of organ system networks, members of cellular networks members of tissue networks a sixth step comprising the selection of a first set of characteristic features of said selected objects and the use of said characteristic features of said selected objects as first intermittent descriptor set of said selected objects.

wherein the first set of characteristic features of said objects are selected from the group comprising proper names and synonyms of objects, symbols for objects, collection of physical properties of objects, collections of measurements associated with objects, unique identifiers of objects in a database a seventh step comprising a sixth method using said first intermittent descriptor set of said objects and using said first, second, third, fourth . . . nth subnetwork descriptor sets of said first selected interaction network system and using said second process of said second step and using said databases for identifying objects capable of interacting directly or indirectly or of exchanging information directly or indirectly with at least one network node of said first, second, third, fourth . . . nth subnetwork system of said first network system and recording the results;

the sixth method may comprise a process using said first set of intermittent object descriptors and said first, second, third, fourth . . . nth set of subnetwork descriptors of said first, second, third, fourth . . . nth subnetwork of said first selected interaction network system and said second process of said second step and said databases for determining coincidence frequencies or coincident measurements of said first set of intermittent object descriptors and said first, second, third, fourth . . . nth subnetwork descriptors of said subnetwork systems of said first selected interaction network system in said database and recording the results, selecting a threshold of said coincidence frequency measurements or coincident measurements for selecting at least one or a plurality of network nodes in said first, second, third, fourth . . . nth subnetwork system of said first interaction network system capable of interacting or exchanging information with said objects;

a tenth process for counting the number of said selected network nodes for said subnetwork systems and said objects and recording the results wherein said results are termed first, second, third, fourth . . . nth object-subnetwork-interaction node counts hereinafter further termed O1-n SN1-n ICN1;

an eight step including a seventh method using said object-subnetwork-interaction node counts termed O1-n SN1-n ICN1 of said objects as numerators and using said subnetwork-node counts termed SN1-nCN1 of said subnetworks of said first interaction network system as denominator for determining the ratio between said subnetwork node counts and recording the result for said objects O1-m and said subnetwork system SN11-n wherein said results, termed normalized first, second, third, fourth object subnetwork-interaction interference scores, are further termed O1-mSN1-n IFSCN1;

a ninth step comprising the recording of said normalized object-subnetwork interaction interference scores O1-mSN1-n IFSCN1 for said subnetwork systems as descriptors of said objects in a database;

a tenth step comprising an eighth method using said object-subnetwork interaction interference scores O1-mSN1-n IFSCN1 and an eleventh process for determining similarities between said object-subnetwork interaction interference scores of said objects and displaying the results;

wherein the eleventh process is selected from the group comprising hierarchical cluster analysis, principal component analysis, vector machines, k means analysis, profile similarity analysis.

The objects may be selected from the group comprising members of social networks, members of financial networks, members of ecologic networks, prescription medicines, over the counter drugs, medicinal herbs, natural products, Ayurvedic medicines, Chinese traditional medicines, Natural medicines, bacteria, algae, Organic and inorganic chemical compositions, Foods, nutrients, vitamins, microorganisms, viruses, supplements, vitamins, mobile devices, patients, clients, communities, members of communities, financial instruments, bonds, companies, members of physiologic networks, members of organ system networks, members of cellular networks members of tissue networks.

The descriptors may be used for determining similarities between information flows induced by said objects or persons in interaction networks, and wherein said interaction networks are selected from the group comprising the internet, social networks, ecologic networks, biologic networks, epidemiologic networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks.

The network systems may be selected from the group comprising epidemiologic networks, biologic communication networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks.

The objects may be selected from the group comprising prescription medicines, traditional medicines, medicinal herbs, foods, natural products, experimental medicines, Ayurvedic medicines, microorganisms, infectious agents.

The coincidence measurements may be selected from the group comprising measurements produced by wearable devices.

DETAILED DESCRIPTION

Previously described methods do not provide novel descriptor sets as described herein and do not allow simultaneous assessment of effects of objects or persons on information flows in multiple interacting dynamic network systems.

Figure 2:
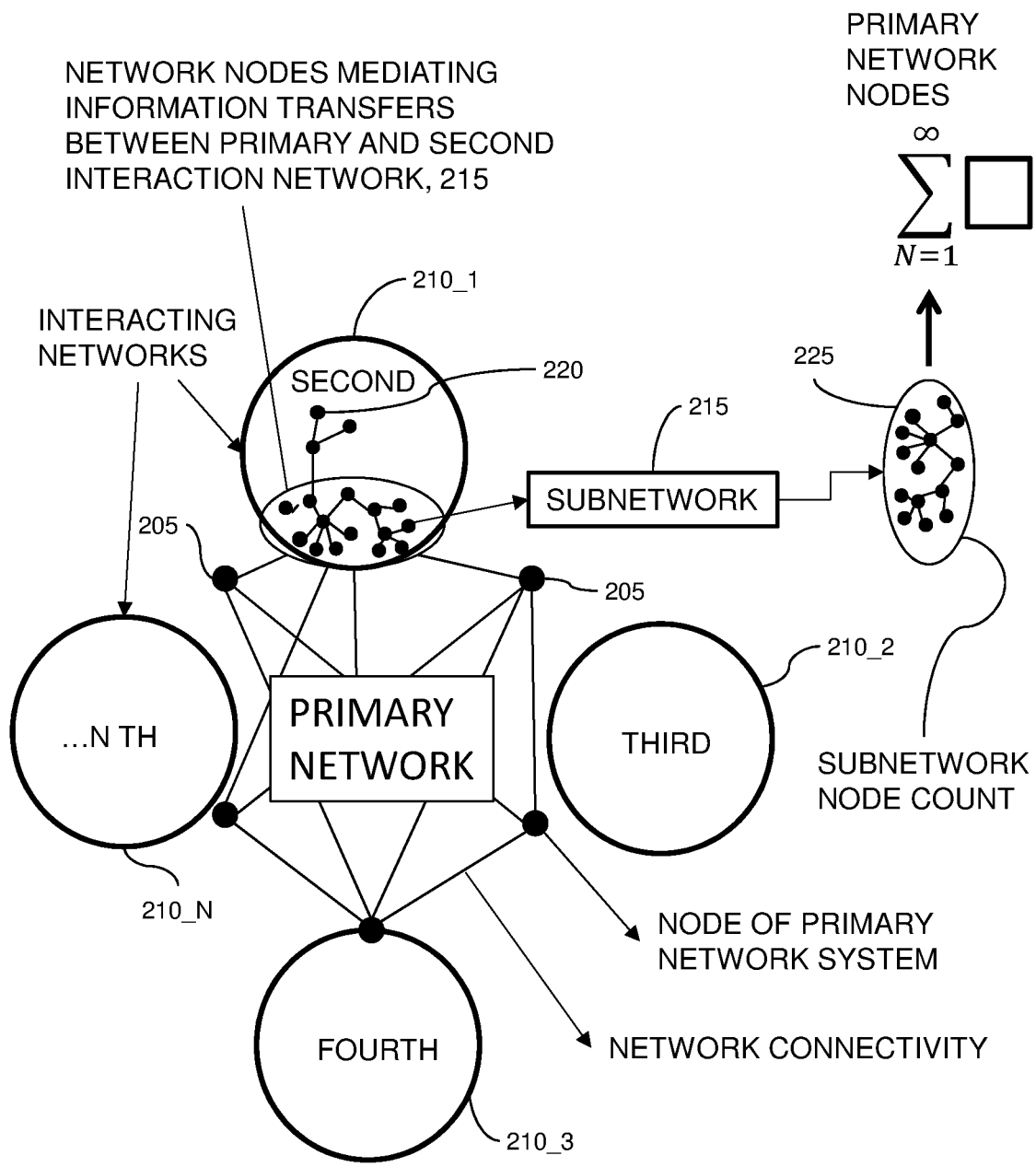
FIGS. 2 through 5 illustrate the exemplary embodiments described herein.
Figure 3:
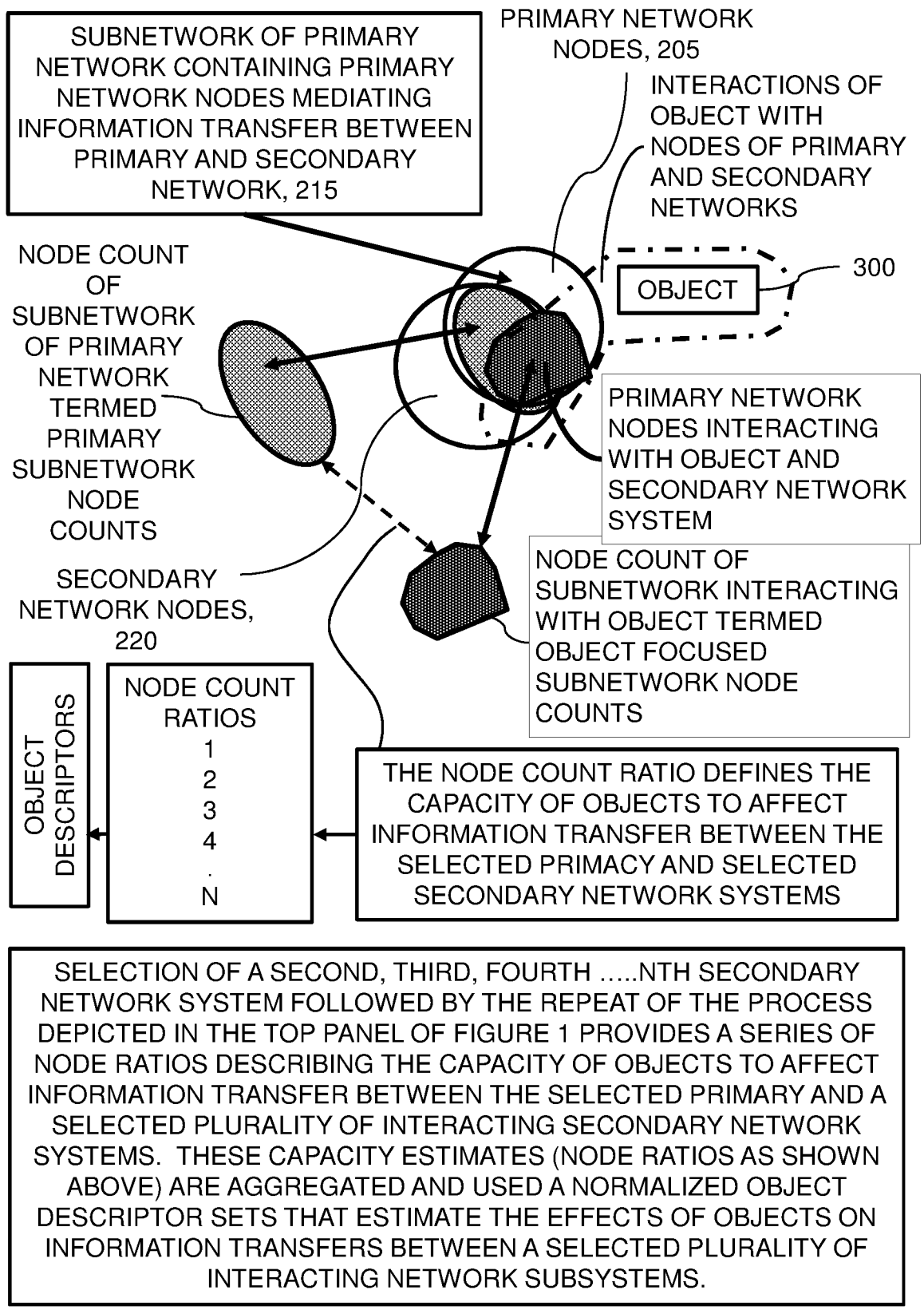
Figure 4:
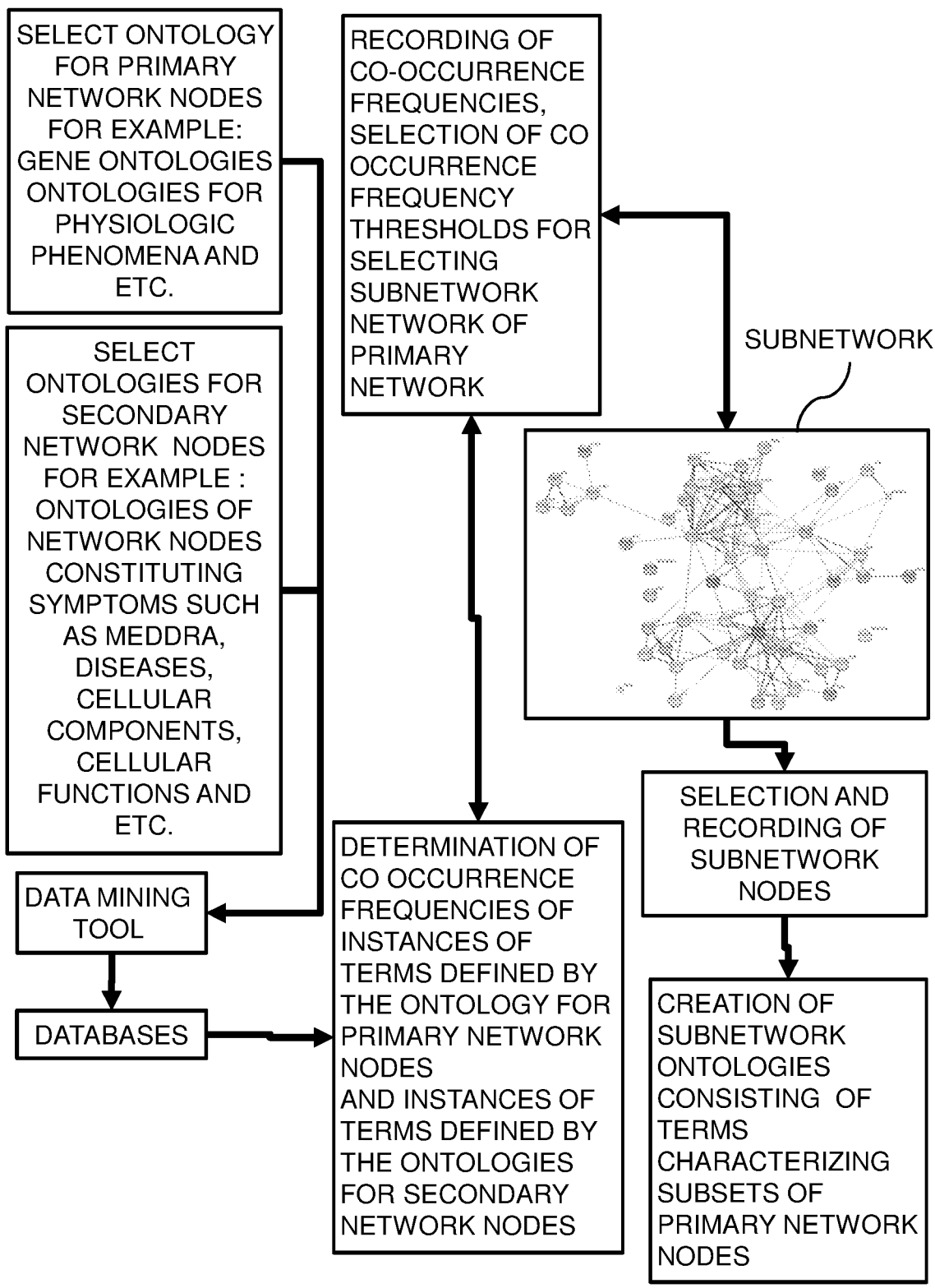
Figure 5:
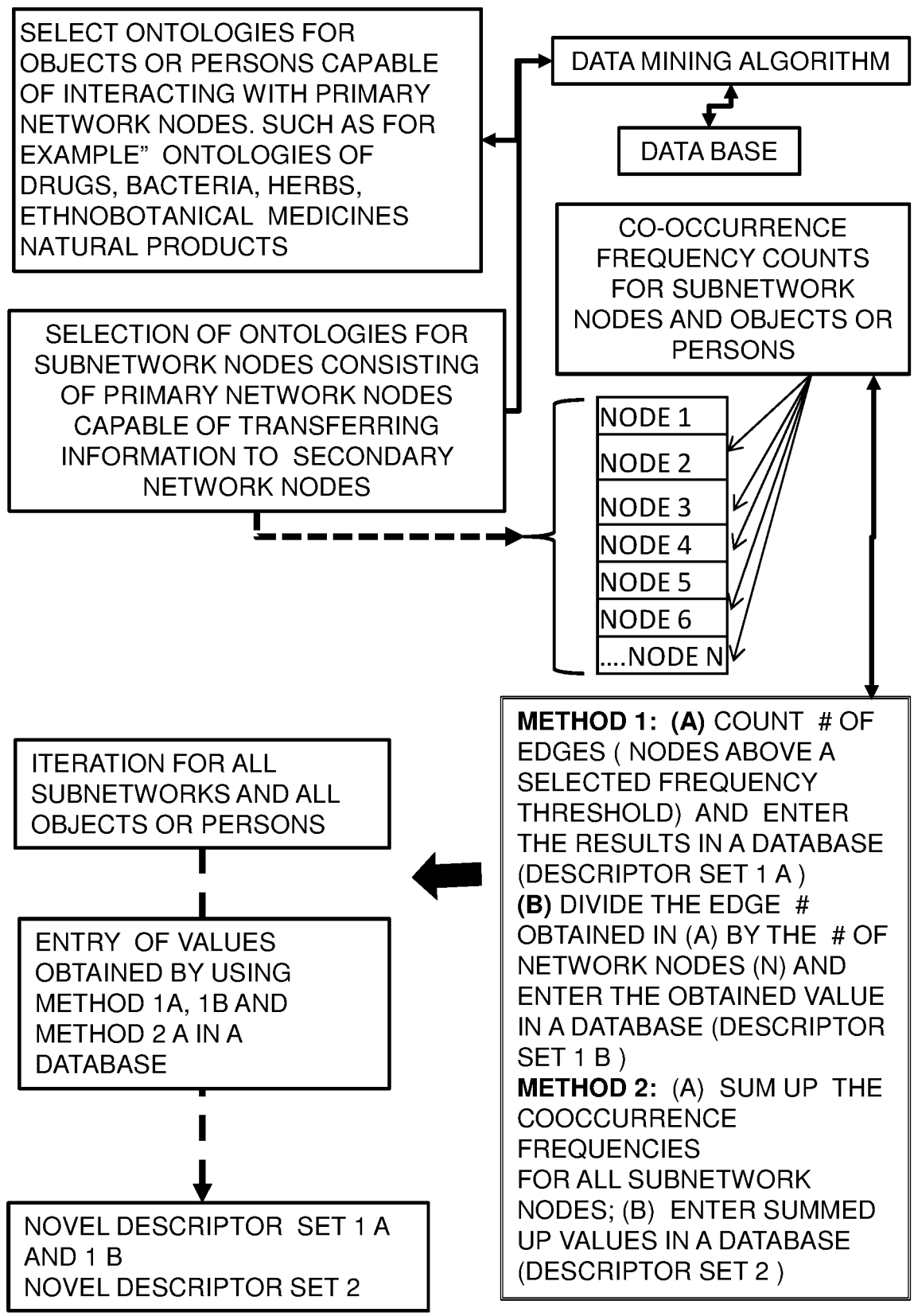

The general scheme of the method used for generating the new descriptor sets of the disclosed embodiments is illustrated in FIGS. 2 and 3. However the configurations shown in these Figures should not be regarded as a limitation of the disclosed embodiments but rather as an illustration of the methodology for constructing the novel descriptor sets because it would be well understood by one skilled in the art that the sequences of the steps shown in the figures and described herein may rearranged in any suitable order and in any number of different ways.

Figure 1:
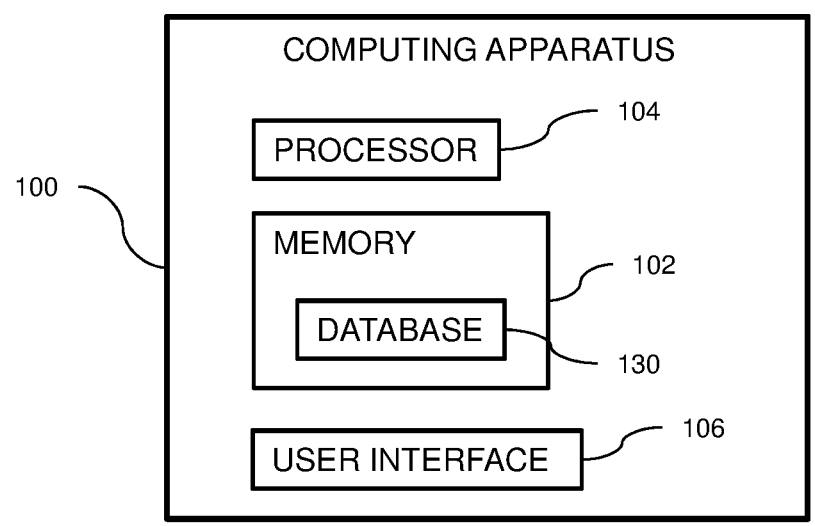
FIG. 1 shows a block diagram of a computing apparatus that may be used to practice aspects of the disclosed embodiment.

In at least one aspect of the disclosed embodiments, the techniques disclosed herein may be executed by one or more computers under the control of one or more programs stored on computer readable medium. FIG. 1 shows a block diagram of an exemplary computing apparatus 100 that may be used to practice aspects of the disclosed embodiment. The apparatus 100 may include computer readable program code stored on at least one computer readable medium 102 for carrying out and executing the process steps described herein. The computer readable medium 102 may be a memory of the computing apparatus 100. In alternate aspects, the computer readable program code may be stored in a memory external to, or remote from, the apparatus 100. The memory may include magnetic media, semiconductor media, optical media, or any media which is readable and executable by a computer. Computing apparatus 100 may also include a computer processor 104 for executing the computer readable program code stored on the at least one computer readable medium 102. In at least one aspect, computing apparatus 100 may include one or more input or output devices, generally referred to as a user interface 106 which may operate to allow input to the computing apparatus 100 or to provide output from the computing apparatus 100, respectively. In at least one embodiment, the memory may include one or more databases 130 as described in detail below.

FIGS. 2 through 5 illustrate an exemplary method for creating descriptor sets for identifying information flows in multiple interacting dynamic network systems according to the disclosed embodiments. The computer processor 104 and the memory 102 including the computer readable program code are configured to cause the computing apparatus 100 to at least perform the methods for creating the descriptor sets disclosed herein.

Referring to FIGS. 2 and 3, the first step of the method for creating the descriptor sets of the disclosed embodiments is the selection of a dynamic network system of interest, referred to as the primary network system 200. The primary network system 200 may be selected from any suitable network system including, without limitation, the internet, social networks, ecologic networks, biologic networks, biologic communication networks, epidemiologic networks, protein networks, supply networks, demand networks, shopping networks, electricity networks, power transmission networks, manufacturing networks, traffic networks, communication networks, wireless networks, financial networks, nutrient networks cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks.

The next step is the selection of characteristic features that identify network nodes 205 of the primary network system 200 that create the network connectivity that mediates the transfer of information or otherwise provide interaction between the selected primary network system 200 and secondary network systems $210_1$-$210_n$. The selected characteristic features may be referred to as the first selected characteristic features.

The first selected characteristic features may be selected from any suitable primary network node features including, without limitation, proper names, synonyms or symbols of network nodes of interaction network systems, measurements associated with network nodes of interaction network systems, a plurality of measurements associated with network nodes of interaction network systems, proper names and synonyms of groups of network nodes of interaction networks, symbols of network nodes of interaction network systems, and symbols of groups of network nodes of interaction network systems.

The next step of the method for creating the descriptor sets according to the disclosed embodiments includes the identification of at least one $210_1$ secondary network system, and for some implementations, a plurality of secondary network systems $210_1$-$210_n$ that are capable of interacting with or exchanging information with the network nodes 205 of the primary network system 200.

The identification of the one or more secondary network systems $210_1$-$210_n$ includes a first process of randomly selecting characteristic features of network nodes of randomly selected interaction networks stored in a database. The randomly selected characteristic features of network nodes of randomly selected interaction networks may be referred to as the second selected characteristic features.

The identification of the one or more secondary network systems $210_1$-$210_n$ also includes a second process of using the first selected characteristic features mentioned above, and the second selected characteristic features for determining coincidence frequencies or coincident measurements of the first selected characteristic features with the second selected characteristic features in a database and recording the results. Coincidence frequencies may generally refer to a number of occurrences where the characteristic features are found in both network nodes, and coincidence measurements may refer to amounts of one or more characteristic features that may coincide between network nodes.

The identification of one or more secondary network systems $210_1$-$210_n$ also includes a third process of using the recorded coincidence frequency or coincidence measurement results for selecting one or more secondary network systems $210_2$-$210_n$ possessing at least one network node capable of interacting with or exchanging information with said primary network system 200.

The secondary network systems $210_1$-$210_n$ may be selected from any suitable network system including, without limitation, the internet, social networks, ecologic networks, biologic networks, nutrient networks, biologic communication networks, epidemiologic networks, protein networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks, military networks, immunologic networks, intelligence networks.

The database 130 may include one or more of any suitable databases, and may be selected, without limitation, from one or more of the Medline database, PubMed databases, EMBL databases, World Traditional Medicine Patent Database, Chinese Traditional Medicine Database, complementary and alternative medicine databases, Wikipedia, collections of digitized publications, measurements collected by surveillance systems, measurements collected by bio-surveillance systems, measurements collected by diagnostic systems, measurements collected by wearable devices, measurements collected by wearable electronic systems, measurements collected by wearable sensors, measurements collected by wearable diagnostic systems, measurements collected through crowd sourcing, medical record databases, adverse event reporting system databases, DHARA databases, and Ayurveda health care system databases.

The next step of the method according to the disclosed embodiments includes subdividing the primary network system 200 into smaller subnetwork systems 215. This subdivision is based on the identification of the network nodes 205 in the primary network system 200 that mediate the transfer of information, or otherwise provide interaction between the primary network system 200 and network nodes 220 constructing the secondary network systems $210_1$-$210_n$. This subdivision of the primary network system 200 into smaller subnetwork systems 215 is accomplished by selecting characteristic features of the network nodes 205 constructing the primary network system 200 and selecting characteristic features of the network nodes 220 constructing the secondary network systems $210_1$-$210_n$ and subsequently using characteristic features of the selected primary network nodes 205 and secondary network nodes 220 for determining coincident measurements or co-occurrence frequency measurements characterizing or indicating interactions or information exchanges between the selected primary network nodes 205 and secondary network nodes 220 in the one or more databases 130 mentioned above and recording the results.

The subdividing step, using coincident measurements or co-occurrence frequency measurements, identifies subnetwork systems 215 of the primary network system 200 that are capable of interacting with or exchanging information with one or more network nodes 220 of the selected secondary network systems $210_1$-$210_n$. This step may be iterated using a plurality of secondary network systems $210_1$-$210_n$ to effect the subdivision of the primary network system 200 into the subnetwork systems 215, wherein each subnetwork system 215 includes a finite number of primary network nodes 205 capable of interacting with network nodes 220 of the selected secondary network systems $210_1$-$210_n$. Each subnetwork system 215 of the primary network system 200 has a specific number of network nodes 205, and that number may be referred to as the primary subnetwork node count 225, and these network nodes 205 determine the dynamic topologies of the respective subnetworks 215 that mediate the transfer of information from the primary network 200 to the selected secondary network systems $210_1$-$210_n$.

Referring to FIG. 3, another step in the creation of the new descriptor sets according to the disclosed embodiments includes in a first selection, the identification of objects 300 that are capable of interacting directly or indirectly or of exchanging information directly or indirectly with network nodes 205 of the primary network system 200. This identification starts out by selecting characteristic features of the objects 300 followed by the determination of co-occurrence frequencies or coincident measurements between the selected characteristic features of the objects and characteristic features of the network nodes 205 constructing the primary network system 200 in the one or more databases 130. It should be understood that the term object may include one or more biological active agents, contagions, persons, or any other item that may interact with one or more network nodes.

Suitable methods for obtaining these co-occurrence frequencies or coincident measurements include the use of text or data mining tools for determining the number of instances where selected characteristics features of objects co-occur with selected characteristic features of the network-nodes 205 of the primary network system 200 found in the one or more of the databases 130 and recording the results. Coincidence measurements may also be obtained by using crowd sourcing for determining coincidence frequency measurements between selected characteristic features of objects and selected characteristic features of network nodes 205 of the primary network system 200 and recording the results. Recording of measurements produced by electronic devices may also be used for determining coincidence frequency or coincidence measurements between selected characteristic features of objects and selected characteristic features of network nodes 205 of the primary network system 200. Likewise, experiments measuring direct or indirect effects of objects on properties of the network nodes 205 of the primary network system 200 may also be used for determining for determining coincidence frequency or coincidence measurements between selected characteristic features of objects and selected characteristic features of network nodes 205 of the primary network system 200. Said measurements are termed object associated coincidence frequency or coincidence measurements for network nodes 205 of the primary network system 200. Said object associated coincidence frequency or coincidence measurements for network nodes 205 of the primary network system 200 are used for selecting subnetworks 215 of the primary network 200 containing subnetwork nodes capable of interacting with selected objects. Likewise said object associated coincidence frequency or coincidence measurements for network nodes 205 of the primary network system are used for selecting objects capable of interacting with subnetwork nodes 215 of the primary network 200.

Method 1

It is well understood to someone skilled in the art that identification and recording of ontologies identifying subnetwork nodes 215 of primary networks 200 has utility in data mining. The capacity of objects to affect information transfer between the selected primary network system 200 and a selected secondary network systems $210_1$-$210_n$ may then be determined in a first process using a text or data mining tool and selecting ontologies of subnetworks 215 of the primary network 200 and by selecting ontologies of objects capable of interacting with said sub network nodes 215 for determining the coincidence frequency or coincidence measurements between instances in said subnetworks ontologies and instances in said object ontologies in said database and recording the result for said cooccurrence frequency or coincidence measurements.

In a second process a threshold for said co-occurrence frequency or coincidence measurements is selected and this threshold is used for determining the number of subnetwork nodes in subnetworks 215 of the primary network 200 which have cooccurrence frequencies or coincidence measurements above said selected threshold and recording the result. Said results termed object reachable subnetwork node counts 235 of subnetworks 215 of primary network 200. Said object reachable subnetwork node counts 235 are also termed edge density measurements 245 for said object and said subnetworks 215 of said primary network 200. Said edge density measurements 245 for said objects and a plurality of selected subnetworks 215 of said primary network 200 are recorded in a database. Said recordings are termed edge density based object descriptors. Said edge density based object descriptors have no units of measurements or scale and provide estimates for the capacity of objects, biological active agents, contagions, persons to affect the transfer of information between selected primary networks and a selected plurality of interacting secondary network systems. Said edge density based object descriptor sets are useful for determining similarities between selected objects and for comparing information flows between objects in a plurality of interacting network systems.

A further aspect of this invention is the normalization of said edge density based object descriptor sets by determining the ratio between said edge density measurements 245 and said subnetwork node counts 225 for said subnetworks 215 of said primary network 200. Said ratio determination includes a step wherein an instance of an object associated edge density measurements 245 is selected as the numerator and an instance of a subnetwork node count 225 of subnetworks 215 of the primary network 200 is selected as the denominator followed by the calculation and recording of the resulting node count ratios. In an alternative embodiment said ratio determination includes a step wherein an instance of an object associated edge density measurements 245 is selected as the denominator and an instance of a subnetwork node count 225 of subnetworks 215 of the primary network 200 is selected as the numerator followed by the calculation and recording of the resulting node count ratios.

Said node count ratios for selected subnetworks 215 are aggregated and used as estimates of the capacity of objects, biological active agents, and contagions, or persons to affect information transfer between selected subnetworks 215 of the selected primary network system 200 and a selected secondary network system $210_1$-$210_n$. For constructing edge density based descriptor for selected objects said node count ratios of objects for subnetworks 215 are aggregated and recorded in a database. Said edge density based descriptors are used to compare the capacity of objects, biological active agents, contagions, persons to affect the transfer of information in a plurality of interacting network systems. Moreover, using the new descriptor set of the disclosed embodiments in hierarchical cluster analysis identifies not only the routing of Information flows induced by "objects or persons" through a plurality of interacting networks but also identifies groups of objects, biological active agents, contagions or persons that induce similar routing of information flows in a plurality of dynamic interacting network systems. Obtaining this information is useful for forecasting responses elicited by objects, biological active agents, contagions or persons in biological systems and dynamic interaction systems.

Method 2

A second embodiment of this invention discloses the creation of second method for creating a second set of new descriptor sets which in includes in a first step the identification of objects, biological active agents, contagions or persons that are capable of interacting directly or indirectly or of exchanging information directly or indirectly with network nodes of the primary network system. This identification starts out by selecting characteristic features of objects, biological active agents, contagions or persons followed by the determination of co-occurrence frequencies or coincident measurements between the selected characteristic features of objects, biological active agents, contagions or persons and characteristic features of network nodes constructing the primary network system in the one or more databases 130 and recording the results.

Suitable methods for obtaining these co-occurrence frequencies or coincident measurements include the use of text mining tools for determining the number of instances where selected characteristics features of objects, biological active agents, contagions or persons co-occur with selected characteristic features of the network-nodes 205 of the primary network system 200 found in the one or more of the databases 130 and recording the results. Coincidence measurements may also be obtained by using crowd sourcing for determining coincidence frequency measurements between selected characteristic features of objects and selected characteristic features of network nodes 205 of the primary network system 200 and recording the results.

Measurements produced by electronic devices determining similar correlations, or experiments measuring direct or indirect effects of objects, biological active agents, contagions or persons on properties of the network nodes 205 of the primary network system 200 and recording the results may also be used.

Once these co-occurrence frequency or coincident measurements are obtained, the number of network nodes may be identified and counted in each of the respective subnetworks 215 of the primary network 200 that are capable of interacting or exchanging information with the selected objects, biological active agents, contagions or persons. The node counts may be referred to as focused subnetwork node counts 235. In the second method for creating a second set of new descriptor sets for objects or persons, the co-occurrence frequency or coincident measurements of objects or persons associated with respective subnetwork node of subnetworks 215 of the primary network 200 are added up and recorded wherein these records identify the sum of cooccurrence frequency measurements for said objects or persons obtained for each subnetworks node of subnetworks 215 of the primary network 200. Said sum of cooccurrence frequency measurements of said objects or persons for said subnetwork node counts 235 of the primary network 200 are referred to as information density measurements of said objects or persons for subnetworks 215 of the primary network 200. Said information density measurements of said objects or persons for subnetworks 215 of the primary network 200 provide estimates of the capacity of objects or persons to affect information transfer between subnetworks 215 of the selected primary network system 200 and the selected secondary network systems $210_1$-$210_n$. These information density determinations have no units of measurements or scale, therefore the information density determinations of objects, biological active agents, contagions, persons obtained for subnetworks 215 of the primary network system 200 may be collected and used, in aggregate, as second new descriptor sets for objects, biological active agents, contagions, persons for tracking the transfer of information induced by these objects, biological active agents, contagions, persons in a plurality of interacting network systems. Moreover, using the second new descriptor set of the disclosed embodiments in hierarchical cluster analysis identifies groups of objects, biological active agents, contagions or persons that induce similar routing of information flows in a plurality of interacting network systems and groups of network topologies regulating similar information flows.

Obtaining this information is useful for forecasting responses elicited by objects, biological active agents, contagions or persons in biological systems.

As an alternate description of the disclosed embodiments, a first method for producing novel descriptors of objects or persons includes:

a first step comprising a means for selecting a first set of characteristic features of network-nodes of a first interaction network system of interest further comprising the use of said selected characteristic features of said network nodes of said first selected interaction network system for creating a first descriptor set of said first interaction network system.

The characteristic features may be selected from the group comprising proper names, synonyms or symbols of network nodes of interaction network systems, measurements associated with network nodes of interaction network systems, a plurality of measurements associated with network nodes of interaction network systems, proper names and synonyms of groups of network nodes of interaction networks, symbols of network nodes of interaction network systems, symbols of groups of network nodes of interaction network systems The interaction network systems may be selected from the group comprising the internet, social networks, ecologic networks, biologic networks, epidemiologic networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks The method may include a second step comprising a second means using said first descriptor set of said first network system for selecting a second, third, fourth . . . nth interaction network system interacting directly or indirectly or exchanging information directly or indirectly with said first interaction network system.

The second means may comprise a first process for randomly selecting characteristic features of network-nodes of randomly selected interaction networks in a databases, a second process using said first descriptor set of said first network system and said randomly selected characteristic features of network nodes of said randomly selected interaction network system for determining coincidence frequencies or coincident measurements of said first descriptor set with said randomly selected characteristic features of network nodes of said randomly selected interaction networks in said database and recording the results further comprising a third process using said recorded results for selecting a second, third, fourth . . . nth interaction network system possessing at least one network node capable of interacting with or exchanging information with said first selected interaction network system.

The database may be selected from the group comprising the Medline database, PubMed databases, EMBL databases, World Traditional Medicine Patent Database, Chinese Traditional Medicine Database, complementary and alternative medicine database, Wikipedia, collections of digitized publications, measurements collected by surveillance systems, measurements collected by bio surveillance systems, measurements collected by diagnostic systems, measurements collected by wearable devices, measurements collected by wearable electronic systems, measurements collected by wearable sensors, measurements collected by wearable diagnostic systems, measurements collected through crowd sourcing, medical record database, adverse event reporting system database, DHARA database, Ayurveda health care system databases.

The second process for determining coincidence frequencies or coincident measurements comprises the selection of an instance of a first descriptor set and the selection of an instance of a second descriptor set and the selection of a database and the use of a text mining means for determining how often an instance of a first descriptor set co-occurs with an instance of a second descriptor set in said database and recording the results; likewise determination of coincidence measurements comprises the selection of an instance of a first descriptor set and the selection of an instance of a second descriptor set and the selection of a data bases and the use of a means for identifying measurements relating an instance of a first descriptor set and an instance of a second descriptor set in said database and recording the results.

The method may further include a third step comprising a third method for selecting a second, third, fourth . . . nth set of characteristic features of network-nodes of said second, third, fourth, nth interaction network system further comprising the use of said second, third, fourth . . . nth set of characteristic features of said network nodes of said second, third, fourth, . . . nth interaction network system for creating a second, third, fourth . . . nth descriptor set of said second, third, fourth . . . nth interaction network system selected in said second step.

The method may include a fourth step comprising a fourth method using said first descriptor set of said first interaction network system and using said second, third, fourth . . . nth descriptor set of said second, third, fourth . . . nth interaction network system and said second process of said second step and said databases for selecting subsets of descriptor sets of said first interaction network systems describing subsets of network nodes of said first interaction network system interacting directly or indirectly or exchanging information directly or indirectly with network nodes of said second, third, fourth . . . nth interaction network system.

The method may further include a fourth process for determining the number of network nodes in said first, second, third, fourth subnetwork system of said first interaction network systems and recording the results wherein said results may be termed first, second, third, fourth . . . nth subnetwork-node counts of said subnetwork system of said first interaction network system are further termed SN1-nCN1

The method may further include a fifth step comprising of a fifth method for selecting a finite set of objects termed O1-m interacting directly or indirectly or exchanging information directly or indirectly with said first interaction network system, wherein said fifth method comprises a fifth process using said first descriptor set of said first interaction network system and using randomly selected characteristic features of randomly selected objects and said second process of said second step and said databases for determining coincidence frequencies or coincident measurements of said first descriptor set with said randomly selected characteristic features of said randomly selected objects in said databases.

The method may further include the selection of coincidence frequency measurements or a coincident measurement threshold and using said threshold for selecting incidences of said coincidence frequency measurements or said coincident measurements for said descriptor sets in said databases and recording the results.

The method may also comprise using said selected coincidence frequency measurements or coincident measurements for selecting objects capable of interacting or exchanging information with at least one or a plurality of network nodes of said first selected interaction network system and recording said selected objects in a database.

The objects may be selected from the group comprising members of social networks, members of financial networks, members of ecologic networks, prescription medicines, over the counter drugs, medicinal herbs, natural products, Ayurvedic medicines, Chinese traditional medicines, Natural medicines, bacteria, algae, Organic and inorganic chemical compositions, Foods, nutrients, vitamins, microorganisms, viruses, supplements, vitamins, mobile devices, patients, clients, communities, members of communities, financial instruments, bonds, companies, members of physiologic networks, members of organ system networks, members of cellular networks members of tissue networks The method may further include a sixth step comprising the selection of a first set of characteristic features of said selected objects and the use of said characteristic features of said selected objects as first intermittent descriptor set of said selected objects.

The first set of characteristic features of said objects may be selected from the group comprising proper names and synonyms of objects, symbols for objects, collection of physical properties of objects, collections of measurements associated with objects, unique identifiers of objects in a database The method may further include a seventh step comprising a sixth method using said first intermittent descriptor set of said objects and using said first, second, third, fourth . . . nth subnetwork descriptor sets of said first selected interaction network system and using said second process of said second step and using said databases for identifying objects capable of interacting directly or indirectly or of exchanging information directly or indirectly with at least one network node of said first, second, third, fourth . . . nth subnetwork system of said first network system and recording the results.

The sixth method may comprise a process using said first set of intermittent object descriptors and said first, second, third, fourth . . . nth set of subnetwork descriptors of said first, second, third, fourth . . . nth subnetwork of said first selected interaction network system and said second process of said second step and said databases for determining coincidence frequencies or coincident measurements of said first set of intermittent object descriptors and said first, second, third, fourth . . . nth subnetwork descriptors of said subnetwork systems of said first selected interaction network system in said database and recording the results.

The method may further comprise the selection of a threshold of said coincidence frequency measurements or coincident measurements for selecting at least one or a plurality of network nodes in said first, second, third, fourth . . . nth subnetwork system of said first interaction network system capable of interacting or exchanging information with said objects. The method may further include a tenth process for counting the number of said selected network nodes for said subnetwork systems and said objects and recording the results wherein said results are termed first, second, third, fourth . . . nth object-subnetwork-interaction node counts hereinafter further termed O1-n SN1-n ICN1.

The method may further comprise an eight step including a seventh method using said object-subnetwork-interaction node counts termed O1-n SN1-n ICN1 of said objects as numerators and using said subnetwork-node counts termed SN1-nCN1 of said subnetworks of said first interaction network system as denominator for determining the ratio between said subnetwork node counts and recording the result for said objects O1-m and said subnetwork system SN11-n wherein said results, termed normalized first, second, third, fourth object subnetwork-interaction interference scores, are further termed O1-mSN1-n IFSCN1.

The method may further include a ninth step comprising the recording of said normalized object-subnetwork interaction interference scores O1-mSN1-n IFSCN1 for said subnetwork systems as descriptors of said objects in a database.

The method may further include a tenth step comprising an eighth method using said object-subnetwork interaction interference scores O1-mSN1-n IFSCN1 and an eleventh process for determining similarities between said object-subnetwork interaction interference scores of said objects and displaying the results.

The eleventh process may be selected from the group comprising hierarchical cluster analysis, principal component analysis, vector machines, k means analysis, profile similarity analysis.

In accordance with the alternate description of the disclosed embodiments, the method for producing novel descriptors of objects or persons may include objects selected from the group comprising members of social networks, members of financial networks, members of ecologic networks, prescription medicines, over the counter drugs, medicinal herbs, natural products, Ayurvedic medicines, Chinese traditional medicines, Natural medicines, bacteria, algae, Organic and inorganic chemical compositions, Foods, nutrients, vitamins, microorganisms, viruses, supplements, vitamins, mobile devices, patients, clients, communities, members of communities, financial instruments, bonds, companies, members of physiologic networks, members of organ system networks, members of cellular networks members of tissue networks.

The descriptors may be used for determining similarities between information flows induced by said objects or persons in interaction networks wherein said interaction networks are selected from the group comprising the internet, social networks, ecologic networks, biologic networks, epidemiologic networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks.

likewise, The object descriptors may be used for determining similarities between objects and persons The network systems may be selected from the group comprising epidemiologic networks, biologic communication networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks.

The objects may be selected from the group comprising prescription medicines, traditional medicines, medicinal herbs, foods, natural products, experimental medicines, Ayurvedic medicines, microorganisms, infectious agents.

The coincidence measurements may be selected from the group comprising measurements produced by wearable devices Various modifications and adaptations may become apparent to those skilled in the relevant arts in view of the foregoing description, when read in conjunction with the accompanying drawings. However, all such and similar modifications of the teachings of the disclosed embodiments will still fall within the scope of the disclosed embodiments.

Furthermore, some of the features of the exemplary embodiments could be used to advantage without the corresponding use of other features. As such, the foregoing description should be considered as merely illustrative of the principles of the disclosed embodiments and not in limitation thereof.

While aspects and variations of the disclosed embodiments have been described herein, it should be understood by those skilled in the art that various changes may be made and equivalents may be substituted for elements thereof without departing from the scope of the disclosed embodiments. Furthermore, the skilled artisan will recognize the interchangeability of various aspects and features from different embodiments. Similarly, the various method steps and features described, as well as other known equivalents for each such methods and feature, can be mixed and matched by one of ordinary skill in the art to construct additional assemblies and techniques in accordance with principles of this disclosure. In addition, many modifications may be made to adapt a particular situation or material to the teachings of the disclosed embodiments without departing from the essential scope thereof. Therefore, it is intended that the disclosed embodiments not be limited to any particular embodiment disclosed as the best mode contemplated for implementing the disclosed structures and techniques, but that the disclosed embodiments will include all features described herein.

The following experiments provide examples of practical applications of the embodiments described herein. Sample portions of the Examples referenced herein are shown below the experiments.

Experiment 1

Method for Creating the Node Ontology for 1456 Disease Term Derived Protein Sub Networks Subnetwork ontologies shown in example A1 were derived using the second process in method 2. Accordingly, the names of 2211 diseases (identifying network nodes in the secondary network) and 14000 gene symbols (identifying 14000 protein network nodes of the primary network) were used for identifying co-occurrence frequencies of instances of disease names and instances of gene symbols in a 2015 version of the Medline databases containing approximately 24 million records of Medline abstracts. The text mining tool used for determining these co-occurrence frequencies was licensed from the university of Connecticut. The resulting co-occurrence frequencies were recorded and a co-occurrence frequency threshold of 5 was selected for the partitioning of network nodes constituting the primary network into protein subnetworks. Selection of a co-occurrence frequency threshold allows to control the number of networks nodes in subnetworks. Regarding data mining applications, sub-networks containing on average less than 100 network nodes and at least 5 network nodes are preferred for constructing information density based descriptor sets. In this experiment, 1456 protein subnetworks were selected by identifying gene symbols that have more than 5 co-occurring instances with a selected disease term in the Medline database and providing subnetworks with at least two network nodes (example A1). As quality control, protein-subnetwork topologies were examined using the STRING database (STRING v10: Nucleic Acids Res. 2015 January; 43: D447-52). If desired, this quality control step may also be used to reduce the number of text mining derived network nodes in protein subnetworks by selecting subnetwork nodes identified in the preceding co-occurrence frequency analysis which achieve the highest confidence level of protein-protein interaction scores in independent protein interaction databases (for example in String v 10 this score is 0.9).

Method for Creating Object Descriptors Using 1456 Information Density Measurement for 6637 Prescription Drugs, Herbs and Natural Medicines and Ontology for 1456 Disease Term Derived Protein Sub Networks (Example A)

The Names and synonyms associated with 6637 prescription drugs, herbs and selected traditional medicines (herein termed objects) and residing in a database stored on a computer were used for determining information density descriptors for the 6637 objects using method 2 and the ontologies identifying the sub-network nodes of 1456 protein sub networks shown in example A1. Again, a 2015 version of approximately 24 million Medline abstracts residing on the same computer and a text mining algorithm licensed from the university of Connecticut was used for determining the information density for each drug, herb and traditional medicine for each of the 1456 protein subnetwork per method 2. The resulting information densities were recorded in a database (see example A2).

Method for Determining Similarities Between Object Descriptors

The information densities measurements of these 6637 objects for these 1456 protein subnetworks and obtained in the previous step (see example A2) were used as object descriptors in UPGMA hierarchical cluster analysis employing as similarity measure cosine correlation and using the "Spotfire software" for data analysis and data visualization.

The resulting similarity matrix identifies the overlap between the 1456 protein subnetworks using as ordering principle similarities between information density measurements for these 6637 objects in 1456 disease based protein-subnetworks. The construction of this similarity matrix identifies information flows induced by biologically active agents in these 1456 protein subnetwork and hence pharmacologic equivalencies between agents. For example, inspecting pharmacology similarities of *Monascus purpureus* indicates that the rice fermentation product "*Monascus purpureus*" shares high information density based descriptor similarities with a group of lipid lowering agents consisting of Bezafibrate, Ezetimibe, Fenofibrate, gemfibrozil, Niacin and Vytorin (a drug combination of Ezetimibe and simvastatin). This grouping of lipid lowering agents shares descriptor similarities within a confidence in cluster similarity value of 0.965 wherein 1 would be the highest similarity value and zero the lowest.

At first this result may seem surprising since lovastatin, which has been isolated from *Monascus purpureus* (Thai Journal of Pharmaceutical Sciences 33(1):39-46•January 2009), shares high information flow similarities with cerivastatin and mevastatin and to a lesser extend with *Monascus purpureus*. However, the clustering of the new descriptors using information densities for 1459 disease network as object descriptors indicates that *Monascus purpureus* has an overall pharmacology profile that differs from that of pure lovastatin. This observation indicates that additional biological active principle constituting this natural medicines contribute to its lipid lowering pharmacology profile. That this observation is indeed correct has been published elsewhere (J. Agric. Food Chem., 2010, 58 (24), pp 12703-12709). For ascertaining the robustness of results obtained through the clustering of the new descriptor sets, the experiment was repeated using two additional information density based object descriptor sets. The first repeat experiments (experiment 2) used information density measurements as object descriptors derived from 975 MedDRA protein sub networks and the second repeat experiments (experiment 3) used 441 information density measurements derived from 441 physiology based protein subnetworks as object descriptors. In addition, these three experiment were repeated by adding objects to analyses (1-3).

Experiment 2
Method for Creating the Node Ontology for 975 MedDRA Term Derived Protein Sub Networks Subnetwork ontologies shown in example B1 were derived using the second process in method 2 and described in experiment 1. Accordingly, the names of 2285 MedDRA terms (identifying network nodes in the secondary network) and 14000 gene symbols (identifying 14000 protein network nodes of the primary network) were used for identifying co-occurrence frequencies of instances of MedDRA terms and instances of gene symbols in a 2015 version of the Medline databases containing approximately 24 million records of Medline abstracts. The text mining tool used for determining these cooccurrence frequencies was licensed from the university of Connecticut. The resulting cooccurrence frequencies were recorded and a co-occurrence frequency threshold of 5 was selected for the partitioning of network nodes constituting the primary network into 975 protein subnetworks. Accordingly, 975 protein subnetworks were obtained containing gene symbols that have more than 5 co-occurring instances with a selected MedDRA term in the Medline database. As quality a control these obtained subnetworks were checked using the STRING database (STRING v10: Nucleic Acids Res. 2015 January; 43:D447-52). This quality control step also allows to prune the number of network nodes by selecting subnetwork nodes obtained through co-occurrence frequency analysis having protein-protein interaction scores with the highest confidence level (0.9).

Method for Creating Object Descriptors Using 975 Information Density Measurement for 6943 Prescription Drugs, Herbs and Natural Medicines and Ontology for 975 MedDRA Term Derived Protein Sub Networks (Example B)

The Names and synonyms associated with 6943 prescription drugs, herbs and selected traditional medicines (herein termed objects) and residing in a database stored on a computer were used for determining information density descriptors for the 6943 objects using method 2 and the ontologies identifying the sub-network nodes of 975 protein sub networks shown in example B1. Again, a 2015 version of approximately 24 million Medline abstracts residing on the same computer and a text mining algorithm licensed from the university of Connecticut was used for determining the information density for each drug, herb and traditional medicine for each of the 975 protein-subnetwork per method 2. The resulting information densities were recorded in a database (see example B2).

Method for Determining Similarities Between Object Descriptors

The information densities measurements of these 6943 objects for these 975 protein subnetworks and obtained in the previous step (example B2) were used as object descriptors in UPGMA hierarchical cluster analysis employing as similarity measure cosine correlation and using the "Spotfire software" for data analysis and data visualization. The resulting similarity matrix identifies the overlap between the 975 protein subnetworks using as ordering principle similarities between information density measurements for these 6943 objects in 975 MedDRA based protein-subnetworks. The construction of this similarity matrix identifies information flows induced by biologically active agents in these 975-protein subnetwork and hence pharmacologic equivalencies between agents. Again, identifying biological active substances sharing MedDRA information density descriptor similarity with *Monascus purpureus* indicates that this rice fermentation product shares high descriptor similarities with a group of lipid lowering agents consisting of Bezafibrate, Ezetimibe, Fenofibrate, gemfibrozil, Niacin and Vytorin (a drug combination of Ezetimibe and simvastatin). This grouping of lipid lowering agents shares descriptor similarities within a confidence in cluster similarity value of 0.973 wherein 1 would be the highest similarity value and zero the lowest.

Experiment 3
Method for Creating the Node Ontology for 441 Physiology Term Derived Protein Sub Networks Example C Subnetwork ontologies shown in example C1 were derived using the second process in method 2 and described in experiment 1. Accordingly, the names of 728 Physiology terms (identifying network nodes in the secondary network) and 5400 gene symbols (identifying 5400 protein network nodes of the primary network most often investigated in the Medline database) were used for identifying co-occurrence frequencies of instances of Physiology terms and instances of gene symbols in a 2015 version of the Medline databases containing approximately 24 million records of Medline abstracts. The text mining tool used for determining these cooccurrence frequencies was licensed from the university of Connecticut. The resulting cooccurrence frequencies were recorded and a co-occurrence frequency threshold of 5 was selected for the partitioning of network nodes constituting the primary network into 441 protein subnetworks. Accordingly, these 441 protein subnetworks contain gene symbols that have more than 5 co-occurring instances with a selected physiology terms in the Medline database. As quality a control these obtained subnetworks were checked using the STRING database (STRING v10: Nucleic Acids Res. 2015 January; 43:D447-52). This quality control step also allows to prune the number of network nodes by selecting subnetwork nodes obtained through co-occurrence frequency analysis having protein-protein interaction scores with the highest confidence level (0.9).

Method for Creating Object Descriptors Using 441 Information Density Measurement for 3431 Prescription Drugs, Herbs and Natural Medicines and Ontology for 441 Physiology Term Derived Protein Sub Networks (Example C)

The Names and synonyms associated with 7420 prescription drugs, herbs and selected traditional medicines (herein termed objects) and residing in a database stored on a computer were used for determining information density descriptors for the 7420 objects using method 2 and the ontologies for 441 physiology term derived protein subnetworks (example C1). Again, a 2015 version of approximately 24 million Medline abstracts residing on the same computer and a text mining algorithm licensed from the university of Connecticut was used for determining the information density for each drug, herb and traditional medicine for each of the 441 protein-subnetworks per method 2. The resulting information densities were recorded in a database. Selecting an information density threshold of 5 provided information density descriptors for 3431 objects each descriptor consisting of 441 information density measurements (see example C2).

Method for Determining Similarities Between Object Descriptors

The information densities measurements for these 3431 objects (example C2) were used as object descriptors in UPGMA hierarchical cluster analysis employing as similarity measure cosine correlation and using the "Spotfire software" for data analysis and data visualization. The resulting similarity matrix identifies the overlap between the 441 protein subnetworks using as ordering principle similarities between information density measurements for these 3431 objects in 441 physiology term derived protein-subnetworks. The construction of this similarity matrix identifies information flows induced by biologically active agents in these 441-protein subnetwork and hence pharmacologic equivalencies between agents. Again, identifying biological active substances sharing information density descriptor similarity with *Monascus purpureus* indicates that this rice fermentation product shares high descriptor similarities with a group of lipid lowering agents again consisting of Bezafibrate, Ezetimibe, Fenofibrate, gemfibrozil, Niacin and Vytorin (a drug combination of Ezetimibe and simvastatin). This grouping of lipid lowering agents shares descriptor similarities within a confidence in cluster similarity value of 0.977 wherein 1 would be the highest similarity value and zero the lowest.

Experiment 4 the fourth experiment involved addition of 695 objects and pertinent disease protein sub network based information density descriptors to the analysis described in experiment 1. Clustering of this expanded descriptor set and identification of objects residing in the group containing the rice fermentation product *Monascus purpureus* (confidence in cluster similarity value 0.97) revealed that this grouping identified in the third experiment contains the same group of lipid lowering agents as identified in experiment 1 and 2 consisting of Bezafibrate, Ezetimibe, Fenofibrate, gemfibrozil, Niacin and Vytorin.

Experiment 5

The fifth experiment involved addition of 400 objects and pertinent medDRA protein sub network based information density descriptors to the analysis described in experiment 2. Clustering of these descriptors and identification of objects residing in the group containing the rice fermentation product *Monascus purpureus* (confidence in cluster similarity value 0.969) reveals that this group contains the same group of lipid lowering agents as identified in experiment 1 and 2 namely Bezafibrate, Ezetimibe, Fenofibrate, gemfibrozil, Niacin and Vytorin.

Experiment 6

The sixth experiment involved addition of 3431 objects and as descriptors the pertinent 441 information density measurements for 441 physiology based protein sub networks to the analysis described in experiment 3. Clustering of these 7420 descriptors and identification of objects residing in the group containing the rice fermentation product *Monascus purpureus* (confidence in cluster similarity value 0.983) reveals that this group contains the same group of lipid lowering agents as identified in experiment 1 and 2 namely Bezafibrate, Ezetimibe, Fenofibrate, gemfibrozil, Niacin and Vytorin.

The Reproducibility of results produced by the clustering of information density based object descriptors (experiments 1-6) shows that the novel descriptor sets of this invention have utility for comparing biological active principles with heterogeneous compositions. These comparisons are not possible with object descriptors used in pharmaceutical drug discovery. Moreover, since the similarities obtained with the novel descriptors are quantifiable, the descriptors of this invention have utility in pharmacological, medical and health research and activities associated with development of pertinent products.

Experiment 7

Method for Creating the Node Ontology for 1652 Physiology Term Derived Disease Sub Networks Subnetwork ontologies shown in example D1 were derived using the second process in method 2. Accordingly, the names of 9350 diseases (identifying network nodes in the secondary network) and the names of 728 physiological phenomena (identifying 728 network nodes of a tertiary network) were used for identifying co-occurrence frequencies of instances of disease names and instances of the names of physiologic phenomena in a 2015 version of the Medline databases containing approximately 24 million records of Medline abstracts. The text mining tool used for determining these cooccurrence frequencies was licensed from the university of Connecticut. The resulting cooccurrence frequencies were recorded and a co-occurrence frequency threshold of 5 was selected for the partitioning of network nodes constituting the primary network into disease subnetworks. The number of network nodes for the resulting disease subnetwork with cooccurrence frequencies above the selected threshold were counted and recorded. Regarding the mining of information associated with biologically active substances, ontologies for sub-networks containing on average less than 50 network nodes and at least 3 network nodes are preferred for constructing information density based object descriptor sets. Accordingly, the ontologies for 1652 disease subnetworks were selected by identifying the terms of physiological phenomena that have more than 5 co-occurring instances with a selected disease term in the Medline database and identify the nodes in pertinent disease subnetworks that have at least three but less than 42 physiologic term based network nodes (example D1).

Method for Creating Object Descriptors Using 1652 Information Density Measurement for 8955 Prescription Drugs, Herbs and Natural Medicines Using the Ontology for 1652 Physiology Term Derived Disease Sub Networks (Example D)

The Names and synonyms associated with 12700 prescription drugs, herbs and selected traditional medicines (herein termed objects) and residing in a database stored on a computer were used for determining information density descriptors for the 12700 objects using method 2 and the ontologies identifying the sub-network nodes of 1652 disease sub networks shown in example D1. Again, a 2015 version of approximately 24 million Medline abstracts residing on the same computer and a text mining algorithm licensed from the university of Connecticut was used for determining the information density for each drug, herb and traditional medicine for each of the 1652 disease subnetwork per method 2. The resulting information densities were recorded in a database (see example D2).

Method for Determining Similarities Between Object Descriptors

The information densities measurements of these 8955 objects for these 1652 disease subnetworks and obtained in the previous step (see example D2) were used as object descriptors in UPGMA hierarchical cluster analysis employing as similarity measure cosine correlation and using the "Spotfire software" for data analysis and data visualization. The resulting similarity matrix identifies the overlap between the 1652 disease subnetworks using as ordering principle similarities between information density measurements for these 8955 objects in 1652 physiology term based disease-subnetworks. The construction of this similarity matrix identifies the information density of these biologically active agents in 1652 disease subnetwork. For example, inspecting the grouping of pharmacologically active gents residing within a confidence in cluster similarity value of 0.971 and containing the rice fermentation product *Monascus purpureus* indicates that "*Monascus purpureus*" shares descriptor similarities with a group of lipid lowering agents including Bezafibrate, Ezetimibe, gemfibrozil, Niacin, Simvastatin, atorvastatin Fluvastatin, Pravastatin Rosuvastatin and allopurinol Experiment 8

Method for Creating the Node Ontology for 472 Anatomy Term Derived Physiologic Networks Subnetwork ontologies shown in example E1 were derived using the second process in method 2. Accordingly, an anatomic ontology consisting of 1159 MESH terms (identifying network nodes in the secondary network) and the names of 728 physiological phenomena (identifying 728 network nodes of a tertiary network) were used for obtaining coincidence measurements of instances of anatomic ontology terms and instances of the names of physiologic phenomena in a 2015 version of the Medline databases containing approximately 24 million records of Medline abstracts. The text mining tool used for determining coincidence measurements for all terms in both ontologies was licensed from the university of Connecticut. The resulting coincidence measurements were recorded and a coincidence measurement threshold of 5 was selected for identifying anatomic terms characterizing network nodes constituting physiologic subnetworks. This coincidence measurements threshold was also used for identifying and recording the number of network nodes in physiologic subnetworks above this threshold. The recording of these subnetwork node counts was used for identifying 472 subnetworks containing between 3 and 200 subnetwork nodes. Mesh terms characterizing these subnetwork nodes were selected for constructing ontologies for 472 physiologic subnetworks to be used in the construction of constructing descriptor sets per method 1 (2 node counts for these 472 sub networks are shown in example E2).

Method for Creating Object Descriptors Using Edge Density Measurement for 16 Objects Consisting of Herbs, Triclosan, and Nutrients Using the Ontology for 472 Anatomy Term Derived Physiologic Networks (Example E1)

The ontology for 6 herbs, triclosan, and 10 nutrients (herein termed objects) and residing in a database stored on a computer were used for determining edge density descriptors for the 16 objects using method 1 and the ontologies characterizing the sub-network nodes of 472 physiologic networks (shown in example E1). Again, a 2015 version of approximately 24 million Medline abstracts residing on the same computer and a text mining algorithm licensed from the university of Connecticut was used for obtaining coincidence measurements for each instance of an object and each instance of a subnetwork node constituting one of the 472 physiologic networks and these results were recorded. A coincidence measurement threshold of 5 was selected and an instance of an object was selected for counting the number of network nodes in each of the 472 subnetworks with coincidence measurements above this threshold. This step was repeated for all objects in the object ontology. For each object the number of network nodes in each of the 472 subnetworks with coincidence measurements above this threshold were recorded. These recordings, termed edge density measurements for these 16 objects (example E3) are used as descriptor sets for these objects. These descriptors can be subjected to further transformation by selecting the edge density measurements obtained for an instance of an object and an instance of a subnetwork and selecting the measurement for the subnetwork node count associated with the selected subnetwork and calculating ratios between these measurements. An example of this transformation is shown in example E4.

Method for Determining Similarities Between Object Descriptors

The edge densities measurements of these 16 objects for these 472 physiologic subnetworks and obtained in the previous step (see example E3) were used as object descriptors in UPGMA hierarchical cluster analysis employing as similarity measure cosine correlation and using the "Spotfire software" for data analysis and data visualization. The resulting similarity matrix identifies the overlap between the 472 physiology subnetworks using as ordering principle similarities between edge density measurements for these 16 objects in 472 anatomy term based physiology-subnetworks. The construction of this similarity matrix identifies the edge density of these 16 biologically active agents in 472 physiology subnetworks.

Experiment 9

Method for Creating the Node Ontology for 2420 MedDRA Term Derived Disease Sub Networks Subnetwork ontologies shown in example F1 were derived using the second process in method 2. Accordingly, the names of 9350 diseases (identifying network nodes in the secondary network) and the names and synonyms of 2285 MedDRA terms diseases (identifying network nodes in the tertiary network) were used for identifying and recording co-incident measurements of instances of disease names and instances of the names and synonyms of MedDRA terms in a 2015 version of the Medline databases containing approximately 24 million records of Medline abstracts. The text mining tool used for determining these co-incident measurements was licensed from the university of Connecticut. The resulting co-incident measurements were recorded. A co-incident measurement frequency threshold of 20 was selected for identifying MedDRA terms characterizing network nodes constituting subnetworks of the selected secondary disease networks. The number of network nodes for the resulting disease subnetwork with cooccurrence frequencies above the selected threshold were counted and recorded. Regarding the mining of information associated with biologically active substances, ontologies for sub-networks containing on average less than 300 network nodes and at least 3 network nodes are preferred for constructing information density based object descriptor sets. Accordingly, the ontologies shown in F1 are useful for identifying ontology subsets with the desired number of network nodes. These ontology subsets are useful for constructing descriptors according to methods 1 and 2.

EXAMPLES

Experiment 1, Example A1, Selected Examples of 1456 Disease Networks

DIS_NTW_pulmonary edema|ACTIN|NODAL|TNF|C3|CRP|CS|PC|MB|ACE|RHO|HP|COIL|CAST|SRC|NOS2|CAD|F2|MPO|ATM|MSC|RHOA|PAH|RPE|NOS3|MAL|PVR|CPE|CXCL1|AQP1|AQP5|

DIS_NTW_Burkitt lymphoma|CD4|ACTIN|NODAL|TNF|C3|FAS|CP|BAX|GC|SRC|CASP3|CD40|TP53|HLA-A|HLA-B|CD44|STAT1|MYC|CDKN1A|EFS|BCL2|BCL2L1|CD19|CPM|CD38|BCR|CD22|LYN|BCL6|CR2|ID3|

DIS_NTW_basal cell carcinoma|ACTIN|FAS|EGFR|MB|BAX|STAT3|CD34|TP53|PTGS2|PCNA|CXCR4|VDR|MDM2|GSTM1|GSTT1|PALM|GSTP1|MAL|BCL2|SHH|MCC|GLI1|ERCC2|SMO|GLI2|GLI3|MC1R|PTCH1|PHLDA1|PTCH2|

DIS_NTW_candidiasis|CD4|TNF|C3|KIT|CS|PC|TG|GCT|STAT3|TLR4|AES|BID|FOXP3|ARC|TLR2|STAT1|NNT|CA3|OTC|AIRE|S100A9|S100A8|CDR2|CDR1|DEFB4A|AMPH|CARD9|

DIS_NTW_alcohol dependence|CD4|AR|COPE|PRL|BDNF|TRH|ADA|FH|NPY|COMT|SLC6A4|CYP2E1|ALDH2|DRD2|SLC6A3|DRD4|ALDH1A1|NKX2-1|ADH1B|TOR1A|ADH1C|THAP1|OPRM1|SGCE|GABRA2|ANKK1|CAMK2A|

DIS_NTW_otitis media|CD4|TNF|C3|CRP|FAS|CP|TG|AR|TH|SDS|HP|TLR4|C2|CAST|BID|NOS2|TLR2|MPO|NHS|NPS|GPT|MYD88|NNT|MUC5AC|ABR|OMP|SPN|MUC5B|PAX9|

DIS_NTW_renal fibrosis|ACTIN|EGFR|TG|ACE|BAX|STAT3|CD68|NOS2|HGF|CD44|CCL2|TGFB1|MSC|SP1|RHOA|MMP2|ANG|SMAD3|CTGF|SIRT1|SMAD2|SMAD4|SPP1|SMAD7|TEC|ACE2|S100A4|BMP7|COL4A3|HK2|

DIS_NTW_nevus|ACTIN|NODAL|KIT|FAS|EGFR|MB|POLE|CD68|TP53|PCNA|SON|BRAF|RPE|CDK4|PALM|CDKN2A|NF1|HRAS|SHH|SLN|PAM|FGFR3|GLI1|NRAS|SMO|MITF|MLANA|MC1R|PTCH1|AMN|

DIS_NTW_abdominal aortic aneurysm|ACTIN|TNF|CRP|CS|CP|PC|EGFR|ACE|CD68|COIL|CAST|CD40|PTGS2|CAD|TF|MTHFR|MPO|NHS|CCL2|APOE|TAT|MMP2|IL10|ANG|MMP9|SACS|SERPINE1|AAAS|LRP1|

DIS_NTW_celiac disease|CD4|ACTIN|TNF|KIT|FAS|PC|TG|MB|SDS|HP|TLR4|PTH|FOXP3|HLA-A|HLA-B|HLA-DRB1|CD14|AGA|CTLA4|HLA-DQB1|HFE|TPO|ACD|OAT|MICA|HLA-DQA1|IL15|IL12A|RGS1|

DIS_NTW_paraplegia|C3|TG|ACE|TH|POLE|HP|COPE|COIL|C2|C6|ATM|RPE|MBP|C5|C7|FES|L1CAM|ALS2|PLP1|SPG11|SPG7|BICD2|BSCL2|CYP7B1|AFG3L2|ATL1|LHB|

DIS_NTW_cholangitis|CD4|ACTIN|NODAL|TNF|CRP|FAS|CP|PC|AR|TLR4|CAST|CD40|PTS|FOXP3|PCNA|HLA-B|HLA-DRB1|ABO|ACR|CFTR|PDC|HLA-C|AIP|MICA|DDC|CLDN1|ABCB4|DLAT|

DIS_NTW_muscular atrophy|ACTIN|TG|MB|BAX|AR|CASP3|SON|C6|C5|CBS|DMD|C7|MOS|PGD|GEM|SOD1|SMN2|TRPV4|SV2A|MAP1B|SNRPN|BICD2|GARS|IGHMBP2|

DIS_NTW_Kaposi's sarcoma|CD4|ACTIN|NODAL|TNF|C3|FAS|BAX|MTOR|STAT3|CD34|SRC|VEGFA|HGF|HLA-A|HLA-B|ARC|TAT|CASP8|RAC1|HLA-C|CD19|CFLAR|CXCR2|CDK6|OSM|IL6ST|SLK|RBPJ|EGLN2|

DIS_NTW_synovitis|CD4|TNF|C3|CRP|CS|GC|RHO|STAT3|TLR4|CD68|CAST|VEGFA|PTGS2|HLA-DRB1|ARC|CD14|MSC|ACR|PALM|HMGB1|IL1RN|GCA|TNFRSF11B|TNFSF11|CD163|PIP|COMP|LARS|

DIS_NTW_pulmonary embolism|NODAL|CRP|CS|CP|PC|EGFR|MB|HP|COIL|CAST|AES|APC|BID|PTS|SI|CAD|MTHFR|NHS|TAT|SCT|PAH|PVR|NNT|CPE|OAT|MIP|SERPINE1|FABP3|

DIS_NTW_invasive carcinoma|CD4|ACTIN|NODAL|EGFR|BAX|AR|CD68|CD34|APC|TP53|NOS2|PTGS2|PCNA|CD44|MYC|BRAF|MUC1|ERBB2|BRCA1|BRCA2|SMAD4|MUC5AC|SLN|MUC2|TP63|ESD|PGR|HGD|MUC6|

DIS_NTW_retinal detachment|CD4|ACTIN|TNF|C3|FAS|CS|PC|POLE|CD68|C2|VEGFA|PCNA|ARC|ERG|GFAP|CLOCK|RPE|PVR|ACD|STAR|VHL|ECD|SPR|SRF|COL2A1|NDP|RLF|

DIS_NTW_myelofibrosis|KIT|MTOR|STAT3|CD34|EPO|CXCR4|TGFB1|SCT|MVD|CXCL12|TPO|BCR|FGFR1|EZH2|FLT3|JAK1|CBL|MPL|IDH1|GATA1|PF4|JAK3|TET2|ASXL1|PDGFRB|SRSF2|CALR|CD177|

DIS_NTW_goiter|CD4|NODAL|KIT|FAS|CS|PC|TG|TH|POLE|SDS|EGF|PTH|PCNA|SON|PRL|TRH|BRAF|RET|CXCL10|SHBG|TPO|DICER1|PAX8|TSHR|SLC26A4|BACH2|DUOX2|

DIS_NTW_ductal carcinoma in situ|ACTIN|NODAL|CS|EGFR|AR|CD68|CD34|TP53|PTGS2|PCNA|CAD|CD44|NHS|ACR|MVD|AKT1|MUC1|ERBB2|BRCA1|NOTCH1|BRCA2|CPM|CCND1|SLN|TP63|CD24|PGR|S100A7|

DIS_NTW_renal carcinoma|ACTIN|NODAL|TNF-|FAS|EGFR|BAX|POLE|MTOR|EGF|PTH|SRC|CD40|APC|DES|EPO|HGF|CXCR4|HIF1A|MDM2|CASP8|IL2|VHL|CFLAR|TSC2|FHIT|CA9|TFE3|PRCC|

DIS_NTW_leukopenia|CD4|NODAL|TNF|C3|CRP|FAS|CS|CP|PC|GC|MTOR|AES|BID|PTS|DES|EPO|MPO|AFP|ERBB2|ADM|MAL|GPT|SARS|GEM|MVP|CD22|TPMT|

DIS_NTW_iron overload|CD4|ACTIN|CRP|FAS|CP|GC|STAT3|SI|EPO|TF|HLA-A|HLA-B|SCT|RPE|HFE|SMAD4|HAMP|CDA|GDF15|BMP6|ALAS2|TFR2|TMPRSS6|FTL|HFE2|HEPH|

DIS_NTW_autosomal recessive disease|CS|MB|ATM|VDR|PAH|BRCA1|CFTR|HFE|AGT|PGD|AIRE|MEFV|NBN|AAAS|GAA|SLC26A4|FANCD2|SMN2|FANCA|FANCC|ABCC6|ABCG8|FANCG|ABCG5|CTNS|DMAP1|GALNS|

DIS_NTW_chondrosarcoma|ACTIN|NODAL|CS|BAX|MTOR|SRC|TP53|PCNA|CD44|CXCR4|MDM2|CTGF|PTK2|RUNX2|CD99|TEC|IDH1|MMP13|EWSR1|SOX9|COL2A1|COMP|IDH2|NR4A3|ADAMTS5|EXT1|EXT2|

DIS_NTW_primary biliary cirrhosis|CD4|ACTIN|TNF|C3|KIT|FAS|AR|TLR4|CD68|CD40|FOXP3|HLA-A|HLA-DRB1|AFP|SP1|VDR|CTLA4|CDKN1A|HLA-DQB1|PML|CD28|TLR9|GPT|PDC|HLA-C|KRT7|DLAT|

DIS_NTW_lymphopenia|CD4|TNF|C3|CRP|FAS|TG|TH|MTOR|AES|FOXP3|CD44|CXCR4|ACR|FASLG|ADA|CD28|TLR9|CD19|SARS|CCR7|CD52|LCK|ATG7|F5|S1PR1|

DIS_NTW_open-angle glaucoma|ACTIN|CS|PC|GC|POLE|RHO|AES|BID|MTHFR|CD44|F2|ERG|APOE|CLOCK|GSTM1|NOS3|GSTT1|DBP|CTGF|ACD|ABCA1|CYP1B1|PSD|NTM|DCT|OPTN|LOXL1|

DIS_NTW_frontotemporal dementia|TG|MB|ACE|POLE|SDS|RAN|APOE|CLOCK|CA1|APP|CBS|INS|SOD1|FUS|PRNP|CDK5|MAPT|VCP|GRN|SQSTM1|LRRK2|PSEN1|PIN1|SNCA|C9ORF72|PSEN2|CHMP2B|

DIS_NTW_late pregnancy|CD4|CRP|CP|TG|ACE|TH|SDS|COPE|PTH|MTHFR|F2|SON|PRL|SP1|ANG|CA1|DBP|AVP|CRH|FOS|CA3|IGF2|POMC|NFKB1|PGF|

DIS_NTW_bone disease|NODAL|TNF|PC|EGFR|TH|SDS|PTH|SRCHGF|MSC|VDR|AGA|CFTR|GLA|TNFRSF11B|TNFSF11|RUNX2|FGF23|PTHLH|CCL3|VIT|DKK1|CTSK|SOST|NFATC1|HPN|LRP5|

DIS_NTW_gastric ulcer|ACTIN|KIT|CP|EGFR|BAX|GC|TH|HP|EGF|COIL|BID|NOS2|PTGS2|PCNA|HGF|MPO|RAN|ABO|NOS3|CBS|LPO|PTGS1|CYP2C19|PGC|TFF3|TFF1|

DIS_NTW_microphthalmia|ACTIN|KIT|MB|STAT3|RPE|SHH|TNFSF11|BMP4|SOX2|HCCS|PAX6|MITF|CTSK|NFATC1|DCT|MLANA|PAX3|SOX10|TFE3|TYRP1|PIAS3|MFRP|BCOR|PITX3|

DIS_NTW_teratoma|ACTIN|NODAL|KIT|CS|PC|TH|POLE|CD34|PTS|AFP|GFAP|VIP|MYC|MSC|BRAF|SCT|EFS|MUC5AC|NES|SOX2|POU5F1|PGC|F9|KLF4|DMRT1|

DIS_NTW_demyelinating disease|CD4|TNF|FAS|TH|CD68|NOS2|FOXP3|HLA-DRB1|CCL2|C6|GFAP|TAT|SP1|CD86|MBP|CCR5|HLA-DQB1|PML|CXCR3|CCR2|APCS|CPM|AQP4|MOG|PLP1|ABCD1|

DIS_NTW_Duchenne muscular dystrophy|ACTIN|MB|ACE|GC|SDS|RHO|C2|SON|TGFB1|ERG|TAT|MSC|CTGF|STAR|DMD|PGD|OTC|PIP|GK|NOS1|AQP4|MYOD1|DAG1|PAX7|MYOG|MSTN|

DIS_NTW_polyneuropathy|CD4|NODAL|TNF|C3|FAS|MB|ACE|COIL|AES|EPO|ARC|SON|NGF|MBP|PALM|FAP|ACHE|ENG|TTR|PNP|DSP|PRNP|NF2|MFN2|MAG|MPZ|

DIS_NTW_irritable bowel syndrome|CRP|CS|AR|COPE|AES|BID|MPO|NHS|VIP|AGA|FH|CIC|CRH|FAP|NNT|CGA|SLC6A4|CCK|TRPV1|OCLN|NMS|FGFR4|GNB3|GAN|TPH1|CNR1|

DIS_NTW_temporal lobe epilepsy|ACTIN|PC|GC|POLE|MTOR|GFAP|BDNF|APOE|CA1|MAL|PGP|NPY|NES|ECD|CA3|PRNP|AQP4|CA2|MAP2|SCN1A|CA4|CALB2|FER|LG1|

DIS_NTW_bladder carcinoma|ACTIN|NODAL|TNF|FAS|EGFR|BAX|STAT3|EGF|SRC|CASP3|CD40|TP53|PTGS2|PCNA|TF|CD44|MYC|MVD|MDM2|TNFSF10|ADM|HRAS|FGFR3|KRT20|PRKCA|UBC|

DIS_NTW_neuritis|CD4|NODAL|TNF|C3|CS|CP|MB|GC|COIL|C2|NOS2|FOXP3|HLA-DRB1|ARC|AFP|CCL2|ERG|GFAP|ATM|MBP|CCR5|MTR|AQP4|MOG|MAG|

DIS_NTW_arteriosclerosis|CD4|ACTIN|C3|CRP|CS|CP|EGFR|TG|ACE|RHO|TLR4|CAST|CD40|NOS2|CADH|GF|MTHFR|TGFB1|APOE|NOS3|ANG|LPL|GLA|GCA|PON1|

DIS_NTW_azoospermia|KIT|MB|AR|MTHFR|SON|PRL|STS|GSTT1|MLH1|CFTR|SHBG|OAT|AMH|SRY|FSHR|SRR|DAZL|CDY1|DAZ2|PRM1|PRM2|

DIS_NTW_cerebral infarction|CD4|CRP|CP|TG|ACE|BAX|TH|POLE|RHO|TLR4|COIL|CASP3|CAD|MTHFR|MPO|GFAP|BDNF|APOE|TAT|VWF|MBP|CA1|ECD|GRASP|ALOX5AP|

DIS_NTW_myositis|CD4|ACTIN|TNF|C3|CRP|FAS|TG|MB|CD68|CAST|HLA-DRB1|CXCL10|ADM|APP|BMP4|HLA-DQA1|BACE1|TTN|EXOSC10|ACVR1|CAPN3|CHD4|CMAS|

DIS_NTW_Barrett's esophagus|NODAL|EGFR|MB|HP|EGF|APC|TP53|NOS2|PTGS2|SI|PCNA|MUC1|CDKN2A|SMAD4|MUC5AC|MUC2|CDX2|KRT20|KRT7|HGD|MUC6|LARS|CDX1|NOX5|

DIS_NTW_brain edema|TNF|TG|BAX|TLR4|VEGFA|EPO|MPO|C6|GFAP|HIF1A|MMP9|CA1|HMGB1|AVP|HMOX1|CA3|C9|S100B|OCLN|AQP4|AQP1|CLDN5|AQP9|

DIS_NTW_familial adenomatous polyposis|ACTIN|BAX|APC|TP53|PTGS2|PCNA|BRAF|RPE|RET|BRCA1|FAP|MLH1|CTNNB1|BRCA2|SMAD4|MSH2|PTGS1|MCC|PGD|DCC|MSH6|PMS2|MUTYH|BMPR1A|

DIS_NTW_acquired immunodeficiency syndrome|CD4|ACTIN|NODAL|TNF|C3|KIT|FAS|PC|TG|POLE|CD68|COPE|CD40|EPO|HLA-B|ARC|CXCR4|TAT|FASLG|CCR5|PML|CCR2|ERAS|DDC|

DIS_NTW_hyperhomocysteinemia|ACTIN|CRP|PC|ACE|APC|CAD|MTHFR|GFAP|APOE|VWF|NOS3|ANG|MMP9|PML|CBS|PON1|COMT|MTR|CYBB|MTRR|BHMT|MMACHC|

DIS_NTW_leukoencephalopathy|CD4|POLE|CD68|EGF|HLA-A|HLA-DRB1|GFAP|TAT|SP1|MBP|HLA-DQB1|PML|MAL|MTR|NOTCH3|NOTCH4|CSF1R|HTRA1|MLC1|TYROBP|

DIS_NTW_dyspepsia|KIT|CP|PC|GC|SDSHP|EGF|AES|BID|PTGS2|SRI|VIP|AGA|FAP|CPM|CBS|SLC6A4|CCK|TRPV1|OTC|PDE5A|GNB3|OCM|

DIS_NTW_spontaneous abortion|CD4|TNF|C3|TH|AES|FOXP3|HLA-A|HLA-

B|HLA-DRB1|MTHFR|F2|AFP|PRL|CTLA4|IL10|HLA-DQB1|CD69|SACS|PGD|HLA-G|HLA-DQA1|CD200|FGL2|
DIS_NTW_papillary thyroid carcinoma|NOD-AL|KIT|FAS|PC|EGFR|TG|POLE|STAT3|APC|CXCR4|BRAF|MUC1|RET|FAP|CTNNB1|HRAS|SLN|NRAS|PAX8|TSHR|HTT|NTRK1|NCOA4|
DIS_NTW_Newcastle disease|CD4|ACTIN|TNF|C3|KIT|CS|CP|TH|SDS|DES|F2|STAT1|CD28|CPE|GAL|FURIN|IRF1|IRF3|IRF7|TBK1|DDX58|IRF2|
DIS_NTW_thalassemia|CD4|CS|PC|TH|SDS|PTH|EPO|HLA-A|SRI|ABO|SCT|PAH|HFE|G6PD|PGD|HAMP|GATA1|ATRX|HBD|BCL11A|HBA2|HBB|
DIS_NTW_keratitis|CD4|ACTIN|KIT|FAS|CS|TG|GC|TLR4|TLR2|MPO|CCL2|RAN|TLR9|MYD88|CPE|ECD|CXCL1|CXCL2|CSK|NTM|AMT|IK|
DIS_NTW_esophagitis|CD4|NODAL|EGFR|TG|HP|EGF|CAST|APC|BID|TP53|PTS|PTGS2|SI|PCNA|FH|TRPV1|GRASP|CDX2|CYP2C19|EDA|CCL26|LARS|
DIS_NTW_urticaria|CD4|TNF|C3|CRP|KIT|ACE|AR|HP|C2|AES|HLA-B|HLA-DRB1|F2|C5|GPT|TPO|ACD|NLRP3|SYK|CD63|NRL|
DIS_NTW_cystitis|ACTIN|TNF|C3|CRP|KIT|CS|CP|EGF|CD34|NOS2|PTGS2|BDNF|SCT|NGF|MIF|GPT|GAL|MCC|TRPV1|UMOD|KRT20|HBEGF|
DIS_NTW_cerebral palsy|CP|PC|SDS|RHO|COPE-|CAST|ARC|APOE|STS|MAX|AGA|PALM|CCS|DMD|C7|MOS|GRASP|ABR|SPR|FES|SLC6A3|CIT|DCD|
DIS_NTW_invasive ductal carcinoma|ACTIN|NODAL|KIT|EGFR|BAX|AR|CD34|TP53|PTGS2|PCNA|CD44|MYC|MVD|MUC1|ERBB2|BRCA1|BRCA2|CCN Experiment 1, Example A, 1456 Disease Network Based Information Desity Descriptors for 6638 Objects drugs
Sum(counts) for 3-methylglutaconic aciduria
Sum(counts) for abdominal aortic aneurysm
Sum(counts) for abetalipoproteinemia
Sum(counts) for acanthosis *nigricans*
Sum(counts) for achalasia
Sum(counts) for achondroplasia
Sum(counts) for achromatopsia
Sum(counts) for acinar cell carcinoma
Sum(counts) for acne
Sum(counts) for acoustic neuroma
Sum(counts) for acquired immunodeficiency syndrome
Sum(counts) for acrodysostosis
Sum(counts) for acromegaly
Sum(counts) for actinic keratosis
Sum(counts) for acute diarrhea
Sum(counts) for acute intermittent *porphyria*
Sum(counts) for acute leukemia
Sum(counts) for acute lymphocytic leukemia
Sum(counts) for acute monocytic leukemia
Sum(counts) for acute myeloid leukemia
Sum(counts) for acute myocardial infarction
Sum(counts) for acute pancreatitis
Sum(counts) for acute promyelocytic leukemia
Sum(counts) for acute pyelonephritis
Sum(counts) for Addison's disease
Sum(counts) for adenocarcinoma
Sum(counts) for adenoma
Sum(counts) for adenosquamous carcinoma
Sum(counts) for adrenal adenoma
Sum(counts) for adrenal hyperplasia
Sum(counts) for adrenocortical carcinoma
Sum(counts) for adrenocortical hyperplasia
Sum(counts) for adrenoleukodystrophy
Sum(counts) for adult respiratory distress syndrome
Sum(counts) for adult T-cell leukemia
Sum(counts) for advanced sleep phase syndrome Experiment 2, Example B, 975 MedDRA Network Based Information Density Descriptors for 6943 Objects Drugs
Sum(counts) for MED_ntw_ABDOMINAL PAIN
Sum(counts) for MED_ntw_ABORTION
Sum(counts) for MED_ntw_ABSCESS Sum(counts) for MED_ntw_ABSENCE SEIZURE
Sum(counts) for MED_ntw_ABUSE
Sum(counts) for MED_ntw_ACANTHOSIS
Sum(counts) for MED_ntw_ACCIDENT
Sum(counts) for MED_ntw_ACHALASIA
Sum(counts) for MED_ntw_ACHE
Sum(counts) for MED_ntw_ACNE
Sum(counts) for MED_ntw_ACROMEGALY
Sum(counts) for MED_ntw_ACUTE CORONARY SYNDROME
Sum(counts) for MED_ntw_ACUTE LEUKEMIA
Sum(counts) for MED_ntw_ACUTE LYMPHOBLASTIC LEUKEMIA
Sum(counts) for MED_ntw_ACUTE MYELOBLASTIC LEUKEMIA
Sum(counts) for MED_ntw_ACUTE RESPIRATORY DISTRESS SYNDROME
Sum(counts) for MED_ntw_ACUTE TUBULAR NECROSIS
Sum(counts) for MED_ntw_ADDICTION
Sum(counts) for MED_ntw_ADENITIS
Sum(counts) for MED_ntw_ADENOMA
Sum(counts) for MED_ntw_ADRENAL INSUFFICIENCY
Sum(counts) for MED_ntw_ADULT RESPIRATORY DISTRESS SYNDROME
Sum(counts) for MED_ntw_AFFECTIVE DISORDER
Sum(counts) for MED_ntw_AGGRESSION
Sum(counts) for MED_ntw_AGITATION
Sum(counts) for MED_ntw_AGRANULOCYTOSIS
Sum(counts) for MED_ntw_AIDS
Sum(counts) for MED_ntw_AKATHISIA
Sum(counts) for MED_ntw_AKINESIA
Sum(counts) for MED_ntw_ALANINE AMINOTRANSFERASE
Sum(counts) for MED_ntw_ALBUMINURIA
Sum(counts) for MED_ntw_ALCOHOL PROBLEM
Sum(counts) for MED_ntw_ALKALOSIS
Sum(counts) for MED_ntw_ALLERGIC CONDITIONS
Sum(counts) for MED_ntw_ALLERGIC REACTION
Sum(counts) for MED_ntw_ALLERGIC RHINITIS
Sum(counts) for MED_ntw_ALLERGY
Sum(counts) for MED_ntw_ALVEOLITIS
Sum(counts) for MED_ntw_AMAUROSIS
Sum(counts) for MED_ntw_AMBLYOPIA
Sum(counts) for MED_ntw_AMENORRHEA
Sum(counts) for MED_ntw_AMNESIA
Sum(counts) for MED_ntw_AMYLOIDOSIS
Sum(counts) for MED_ntw_ANAPHYLAXIS Sum(counts) for MED_ntw_ANEMIA
Sum(counts) for MED_ntw_ANEURYSM
Sum(counts) for MED_ntw_ANGER Experiment 2, Example B1, Selection from 975 MedDRA Term Based Protein Subnetworks MED_ntw_NECK PAIN|CRP|C3|C2|C6|C5|C7|LBP|CNP|
MED_ntw_LARYNGEAL CANCER|NODAL|EGFR|BAX|PCNA|MVD|CD44|GSTM1|GSTT1|CCND1|
MED_ntw_KELOID|ACTIN|FAS|MTOR|TGFB1|SMAD3|SMAD2|CTGF|SMAD4|SMAD7|
MED_ntw_BUNDLE BRANCH BLOCK|CS|NODAL|MB|CAD|PTS|MAX|MPI|SCN5A|DSE|
MED_ntw_AORTIC REGURGITATION|ACE|AR|CAD|AVP|HLA-B|MVP|ESD|RHD|
MED_ntw_CANCER PAIN|CP|COPE|AES|CLOCK|MSC|TRPV1|NNT|CPM|BPI|
MED_ntw_LYMPHOCYTOSIS|CD4|TNF|NODAL|FAS|HP|CD19|CD38|CD5|
MED_ntw_MYCOBACTERIAL INFECTION|CD4|TNF|NOS2|TLR4|TLR2|STAT1|MYD88|NTM|
MED_ntw_HEPATIC DAMAGE|ACTIN|FAS|BAX|NOS2|MPO|GPT|CCL4|CYP2E1|
MED_ntw_SLEEP DISTURBANCE|CD4|CRP|CP|AR|COPE|CLOCK|ACR|MOS|TST|
MED_ntw_ZINC DISORDER|CD4|CRP|ACE|CASP3|RPE|SLC39A1|SLC39A4|
MED_ntw_AKATHISIA|TH|AES|NNT|CYP2D6|PTPRD|MAP2K5|MEIS1|BTBD9|
MED_ntw_ICHTHYOSIS|CS|TG|MB|STS|FLG|SPINK5|ABHD5|ABCA12|
MED_ntw_HYPOTONIA|CP|MB|SON|MECP2|GAA|RYR1|ACTA1|SNRPN|
MED_ntw_SYNDACTYLY|MB|SON|SHH|FGFR2|FGF8|GJA1|GLI3|HOXD13|
MED_ntw_SKIN DISORDER|CD4|ACTIN|MAL|ATP2A2|DSG3|COL7A1|SPINK5|ATP2C|
MED_ntw_OPTIC ATROPHY|MB|POLE|ERG|OPA1|MFN2|OPA3|DNM1L|PRPS1|
MED_ntw_EXFOLIATION|ACTIN|PC|CAST|GC|MICA|AFM|LOXL1|
MED_ntw_VIRILISATION|AR|SHBG|SRY|POR|CYP19A1|SRD5A2|CYP11B1|CYP21A2|
MED_ntw_PELVIC PAIN|CP|CS|KIT|NGF|TRPV1|PGP|SCN11A|P2RX3|
MED_ntw_ALKALOSIS|PTH|CA1|ALK|CDA|SLC12A3|SLC26A4|CLCNKB|
MED_ntw_POLYURIA|PTH|AVP|AQP4|AQP1|AQP2|AQP3|SLC12A1|AVPR2|
MED_ntw_AUTONOMIC NEUROPATHY|CAD|EPO|NGF|FAP|TTR|HBA1|WNK1|NTRK1|
MED_ntw_HYPERURICEMIA|CRP|ACE|TG|EGFR|CAD|UMOD|ABCG2|SLC2A9|
MED_ntw_RENAL CYST|POLE|EGFR|MTOR|SRC|CFTR|VHL|PKD1|PKD2|
MED_ntw_FIBROCYSTIC BREAST DISEASE|ACTIN|NODAL|COIL|EGF|PRL|TRH|PIP|MGA|
MED_ntw_RESPIRATORY INFECTION|CD4|CRP|TH|KIT|AHR|SARS|PIK3CD|
MED_ntw_NEPHROSIS|C3|ACTIN|ACE|TG|AFP|RARA|NPHS2|
MED_ntw_KNEE PAIN|POLE|AES|RHO|NHS|RAN|TF|ACR|KL|
MED_ntw_PRECOCIOUS PUBERTY|TH|SDS|PRL|PAH|TRH|FH|IPP|KISS1|
MED_ntw_VASCULAR DISORDER|ACTIN|ACE|COIL|CAD|VWF|NOS3|ENG|ACVRL1|
MED_ntw_TETRALOGY OF FALLOT|NODAL|COIL|TF|PVR|LPA|MPI|GATA4|NKX2-5|
MED_ntw_MANIA|POLE|AES|CLOCK|BDNF|TRH|SLC6A4|BPI|AMPH|
MED_ntw_MOTOR DYSFUNCTION|CP|TG|POLE|BDNF|GFAP|GDNF|SOD1|HTT|
MED_ntw_EXOPHTHALMOS|ACTIN|CS|COIL|CD34|TRH|ECD|CD99|
MED_ntw_ANGIOPATHY|ACTIN|TG|APOE|APP|CST3|NOTCH3|PRNP|PSEN1|
MED_ntw_TARDIVE DYSKINESIA|HP|BDNF|CYP2D6|CYP1A2|HAL|DBH|DRD2|DRD3|
MED_ntw_CATALEPSY|CP|TH|POLE|GC|F2|FOS|HAL|DRD3|
MED_ntw_PHOTOTOXICITY|ARC|C6|PAH|NPS|RPE|HPD|CPZ|
MED_ntw_DELIRIUM|CRP|COPE|CLOCK|APOE|NMS|S100B|AMT|SLC6A3|
MED_ntw_RENAL INTERSTITIAL FIBROSIS|ACTIN|ANG|HGF|TGFB1|SMAD3|SMAD2|CTGF|SMAD7|
MED_ntw_HOSTILITY|CRP|COPE|CAD|SI|PRL|TAT|DBP|CORT|
MED_ntw_ESOPHAGEAL CARCINOMA|NODAL|FAS|EGFR|BAX|EGF|PCNA|MVD|ESD|
MED_ntw_LYMPHADENITIS|CD4|CRP|NODAL|FAS|CD68|GPT|NTM|
MED_ntw_HEPATOCELLULAR DAMAGE|TNF|ACTIN|FAS|TLR4|STAT3|HMGB1|CCL4|
MED_ntw_CONJUNCTIVITIS|C3|KIT|AR|AES|BID|ARC|ACD|
MED_ntw_NECROTIZING ENTEROCOLITIS|CRP|TNF|NOS2|TLR4|EGF|AGA|INT|
MED_ntw_POLYARTHRITIS|CD4|CRP|C3|TNF|ACR|HLA-B|HLA-DRB1|
MED_ntw_ARTERIAL THROMBOSIS|CRP|PC|CAD|TF|APC|VWF|MTHFR|
MED_ntw_DENTAL CARIES|CD4|CP|CS|COPE|GC|NHS|SRI|TF|
MED_ntw_CARDIOGENIC SHOCK|CRP|CS|NODAL|ACE|MB|PTS|DES|
MED_ntw_PORPHYRIA|AIP|HFE|CYP1A2|DDC|ALAD|ALAS2|HMBS|
MED_ntw_CONNECTIVE TISSUE DISORDER|MVP|COL1A1|COL1A2|FBN1|COL3A1|COL5A1|ABCC6|
MED_ntw_MALIGNANT HYPERTHERMIA|NMS|HAL|RYR2|RYR1|CACNA1S|CASQ|

MED_ntw_KERATOPATHY|ACTIN|PC|PVR|ECD|AMT|PAX6|PBK|
MED_ntw_HEPATOSPLENOMEGALY|CD4|NODAL|FAS|CD5|CD7|NPC1|NPC2|
MED_ntw_ACANTHOSIS|SHBG|LMNA|FGFR3|FGFR2|INSR|BSCL2|
MED_ntw_GALLSTONES|PC|TG|CCK|CYP7A1|ABCB4|ABCG8|
MED_ntw_POLYMYOSITIS|CD4|C3|TNF|MB|HLA-DRB1|DMD|EXOSC10|
MED_ntw_DESQUAMATION|SARS|KLK5|SPINK5|DSG1|CDSN|
MED_ntw_PEELING|ACTIN|POLE|ERG|RPE|PVR|AFM|CDSN|
MED_ntw_HYPOALBUMINEMIA|CD4|CRP|C3|EGFR|PTH|ALB|APTX|
MED_ntw_OPTIC NEUROPATHY-|POLE|ERG|MTHFR|GCA|PSD|OPA1|OPA3|
MED_ntw_EPIDERMAL NECROLYSIS|CD4|FAS|HLA-B|HLA-A|FASLG|CYP2B6|GNLY|
MED_ntw_PLEURAL MESOTHELIOMA|NODAL|EGFR|MTOR|VEGFA|MSC|ERCC1|REN|
MED_ntw_MUSCLE INJURY|ACTIN|MB|DMD|MYOD1|PAX7|MYOG|
MED_ntw_STILLBIRTH|CD4|CS|COPE|NHS|AFP|FGR|

Experiment 3 Example C Descriptors for 3989 Objects Derived from Information Density Measurement of 441 Physiology Term Derived Protein Subnetworks

| physilogy derived protein sub-networks | objects information | desinsity measurements |
|---|---|---|
| PHYSIOL_NETW_CD4 | 5-azacitidine | 6 |
| PHYSIOL_NETW_Oogenesis | 5-azacitidine | 5 |
| PHYSIOL_NETW_Organogenesis | 5-azacitidine | 7 |
| PHYSIOL_NETW_Orientation | 5-azacitidine | 9 |
| PHYSIOL_NETW_Ovulation | 5-azacitidine | 7 |
| PHYSIOL_NETW_Phagocytosis | 5-azacitidine | 7 |
| PHYSIOL_NETW_Platelet Count | 5-azacitidine | 5 |
| PHYSIOL_NETW_Puberty | 5-azacitidine | 5 |
| PHYSIOL_NETW_Pulse | 5-azacitidine | 8 |
| PHYSIOL_NETW_Remission | 5-azacitidine | 9 |
| PHYSIOL_NETW_Reproduction | 5-azacitidine | 11 |
| PHYSIOL_NETW_Respiration | 5-azacitidine | 8 |
| PHYSIOL_NETW_Running | 5-azacitidine | 9 |
| PHYSIOL_NETW_Sensation | 5-azacitidine | 6 |
| PHYSIOL_NETW_Sleep | 5-azacitidine | 8 |
| PHYSIOL_NETW_Spermatogenesis | 5-azacitidine | 13 |
| PHYSIOL_NETW_Swimming | 5-azacitidine | 5 |
| PHYSIOL_NETW_VentricularFunction | 5-azacitidine | 5 |
| PHYSIOL_NETW_Vision | 5-azacitidine | 7 |
| PHYSIOL_NETW_Weaning | 5-azacitidine | 8 |
| PHYSIOL_NETW_WeightGain | 5-azacitidine | 7 |
| PHYSIOL_NETW_WoundHealing | 5-azacitidine | 9 |
| PHYSIOL_NETW_CD4 | Abacavir | 51 |
| PHYSIOL_NETW_Oocysts | Abacavir | 171 |
| PHYSIOL_NETW_Oogenesis | Abacavir | 8 |
| PHYSIOL_NETW_Organogenesis | Abacavir | 179 |
| PHYSIOL_NETW_Orientation | Abacavir | 323 |
| PHYSIOL_NETW_Osteogenesis | Abacavir | 178 |
| PHYSIOL_NETW_Osteolysis | Abacavir | 17 |
| PHYSIOL_NETW_Overweight | Abacavir | 196 |
| PHYSIOL_NETW_Ovulation | Abacavir | 190 |
| PHYSIOL_NETW_Pain Threshold | Abacavir | 7 |
| PHYSIOL_NETW_Parity | Abacavir | 170 |
| PHYSIOL_NETW_Partial Thromboplastin Time | Abacavir | 188 |
| PHYSIOL_NETW_Parturition | Abacavir | 9 |
| PHYSIOL_NETW_Peak Expiratory Flow Rate | Abacavir | 9 |
| PHYSIOL_NETW_Peripheral Tolerance | Abacavir | 169 |
| PHYSIOL_NETW_Phagocytosis | Abacavir | 204 |
| PHYSIOL_NETW_Physical Fitness | Abacavir | 170 |
| PHYSIOL_NETW_PlasmaVolume | Abacavir | 11 |
| PHYSIOL_NETW_Platelet Aggregation | Abacavir | 50 |
| PHYSIOL_NETW_Platelet Count | Abacavir | 306 |
| PHYSIOL_NETW_PlateletActivation | Abacavir | 193 |
| PHYSIOL_NETW_Postpartum Period | Abacavir | 166 |
| PHYSIOL_NETW_Posture | Abacavir | 6 |
| PHYSIOL_NETW_Pregnancy Outcome | Abacavir | 285 |

Experiment 3, Example C1, Ontology for Nodes in
441 Physiology Term Based Protein Subnetworks PHYSIOL_NETW_Thermogenesis|PPARGC1A|NPY|TRH|LCT|LPL|COPE|PRDM16|TEFHP|FOS|ARC|DIO2|FAS|TRPV1|CRH|CIT|BMP8B|TG|TH|AGRP|MTOR|FGF21|TNF|POMC|COIL|SLC2A4|MC4R|CIDEA|ANG|SLN|STAT3|ADRB3|CS|GC|PYY|TES|FABP4|NTS|CLOCK|AVP|TRPM8|FABP7|MPO|CPI|GF2|AR|BDNF|CAST|RAN|MB|MAX|MUSK|BMP7|ATF4|RARA|GPR50|ACOT13|

PHYSIOL_NETW_Theta Rhythm|CA1|CA3|RAN|MPO|BDNF|ACHE|HCN1|

PHYSIOL_NETW_Thinness|BID|ACTIN|RAN|PY-Y|AR|SRI|

PHYSIOL_NETW_Thrombin Time|VWF|TAT|FGG|FGB|PC|CS|TF|PROC|FGA|PF4|CRP|C3|MAX|APC|PLG|FDPS|

PHYSIOL_NETW_Thrombopoiesis|TPO|MPL|MEIS1|DNM3|EPO|ACTIN|KIT|CD4|GC|SRC|GATA1|

PHYSIOL_NETW_Tidal Volume|PIP|MAX|PC|CS|TANK|PPL|C2|MIP|RHO|MPO|SI|CXCL2|NTS|ACE|TLR4|PVR|ACTIN|CP|TNF|DMD|C3|RAN|CAST|SACS|ANG|TH|AR|VIP|LTF|C5|SRC|PALM|COIL|RPE|FH|EPO|COPE|ATM|ASL|C7|FEV|RARS|SARS|MB|CAD|PNP|IDS|TRH|NOS2|ACD|NMS|DSP|HMGB1|HAL|CXCL1|COPA|MEFV|ACHE|MBP|NODAL|FOS|TRPV1|DES|HP|CAPS|CCK|C6|ATR|FES|MIF|CPD|CTRL|MYD88|AIP|SKI|CFB|CTGF|STRAP|VCP|PGD|CD14|

PHYSIOL_NETW_Tooth Eruption|EGF|TNFRSF11B|RUNX2|CAST|BMP6|PTH1R|TNFSF11|BMP2|DMP1|

PHYSIOL_NETW_Torpor|COPE|CLOCK|GPR50|NPY|CA1|CA3|PTMS|

PHYSIOL_NETW_Total Lung Capacity|MEFV|MIP|FEV|ARC|MAX|PAH|ACE|AHR|CAD|COIL-|CRP|PC|SARS|HP|SCT|TG|

PHYSIOL_NETW_Touch|SI|GRASP|PALM|SLN|COPE|PC|NODAL|CP|PREP|KIT|NHS|PIEZO2|CS|C3|TANK|ACTIN|FOS|POLE|RET|COIL|C2|TH|HP|CAST|TRPV1|CAPS|SP6|ARC|AR|C5|RAN|C6|STAR|DCD|TG|C7|CLOCK|AFM|APP|NUMB|CD4|RHO|STS|EGF|NGF|NPS|TRPV4|CD68|SMS|PIEZO1|CAD|SCT|VIP|PGP|EGFR|RPE|F2|ADA|ECD|CCND1|MYCN|MAX|ACE|SDS|CA1|PRL|SON|MB|HMGB1|ACHE|DES|DBP|TES|PTGS2|MCC|APOE|GAN|SP1|TP53|DST|DCN|SP2|CTBS|ACR|ATOH1|

PHYSIOL_NETW_Transplantation Tolerance|CD40|CD4|FOXP3|CTLA4|DST|FAS|CD28|CD86|APCS|TNFRSF18|CP|VDR|TLR4|APC|STAT3|MYD88|TLR9|CD80|CD274|

PHYSIOL_NETW_Tropism|CCR5|CD4|CXCR4|CD46|CLMP|MSC|SI|SARS|TAT|CD81|ACTIN|CCR3|C6|PML|CCR2|C3|STAT1|TNFRSF4|PAM|CXCL12|SLC9A2|CDR1|FAS|TNF|EGFR|RPE|CPE|FURIN|CR2|CD40|CP|C2|GC|CD5|CD163|PVR|ERBB2|CXCR2|CCR9|APC|NODAL|EGF|DES|ACE2|APOBEC3G|CTAGE1|TG|CXCR6|PC|APOE|GFAP|CCR7|CCL2|FGF2|CD44|MLN|CLDN1|IFIH1|CEACAM1|CLEC4M|STAT3|TH|DMD|SRC|CD69|PALM|COPE|POLE|CD68|SACS|CD14|CFTR|HGF|GALT|RAC1|CX3CR1|CCL25|OCLN|TMPRSS2|CS|CD86|APCS|MTOR|CD2|PDC|HP|CAST|F2|SP1|F3|NES|VWF|JUN|FYN|GSC|TNFSF11|EPO|VEGFA|CCR4|CR1|CCL28|CX3CL1|CXCR3|CCR8|APOB|PARVA|F11R|CCL5|APOC3|DDX58|TNFSF10|APOC2|CCR10|RCVRN|ROBO4|EPHA2|YBX1|GRR1|

PHYSIOL_NETW_Tumor Escape|FAS|HLA-G|FASLG|EBAG9|KLRK1|HLA-A|MLANA|PMEL|EGFR|CTLA4|CD274|PDCD1|TAP2|CD4|STAT3|CD86|APCS|FOXP3|TLR4|MICA|HLA-B|HLA-C|CXCR4|ACTIN|CXCL12|CD40|APC|IL10|CD59|PSCA|MICB|MAGEA3|

PHYSIOL_NETW_Urination|PVR|PC|CP|CIC|ARC|PRUNE|COPE|TH|COIL|MAX|AVP|C2|PALM|POLE|RHO|BCR|DES|F2|ACHE|AES|GPT|SI|C6|NGF|AQP2|S100B|CD4|NODAL|PDE5A|AGA|NPS|NHS|TRPV1|RAN|DCD|SDS|BID|

PHYSIOL_NETW_Urodynamics|LPP|CIC|PVR-|RHO|MCC|BCR|NGF|ALPP|PRUNE|IPP|PC|ARC|

PHYSIOL_NETW_Uterine Contraction|F2|PGF|SP6|PHYSIOL_NETW_Vaccine Potency|APCS|BCL2D|KIT|PHYSIOL_NETW_Valsalva Maneuver|MB|SI|CLPP|PALM|NODAL|CAD|

PHYSIOL_NETW_Vascular Remodeling|PAH|ANG|ACTIN|NOS3|ACE|RHO|BMP4|ID1|MMP2|BMPR2|VEGFA|CRP|RHOA|STAT3|ID3|RAC1|EGFR|HIF1A|PCNA|PVR|TGFB1|NOX4|CTGF|SPP1|CAD|MMP9|TNF|ENG|EGF|SRC|SMAD2|NOTCH1|NOS2|SACS|LPA|BAX|FAS|CASP3|CXCL12|ACE2|MTOR|PTGS2|AR|TF|CXCR4|FLT1|CCL2|EPHB4|TRPC6|SOD1|CCR2|EPHA2|CNP|SMAD3|NOTCH4|CD4|CD40|CX3CD|EGR1|SLC6A4|GK|APLN|ANGPT1|COIL|NODAL|ARC|HMGB1|PC|C3|PDE5A|CD68|VIP|AHR|CX3CR1|VWF|SMAD1|TPH1|LOX|NOX1|APLNR|CDK2|DES|PLAUR|TPR|FH|COPE|TG|TRPC4|CD34|TLR4|CEACAM1|CCL5|SP1|EPO|CD36|HMOX1|CXCL1|LCN2|FOXO1|PRKG1|PTK2|CYBB|DLL4|SYK|UNK|TIE1|PDE1C|NGF|GFAP|AVP|MB|DBP|TRPV4|SRF|NOS1|INS|HLA-G|ERBB2|BCL2|PTX3|AKT1|TAT|APOE|CD14|CXCR3|AXL|NFATC2|PTGS1|SGK1|MIF|CTSK|CFD|AQP1|ADAM17|TAL1|ANXA5|TRPM7|SLC9A1|LRP1|ERBB4|RGS2|CDK4|SMAD4|UTS2R|SOD2|VHL|SMARCA4|GREM1|BIRC5|GATA6|PTK2B|TEK|FBLN5|HEY2|MEOX2|

PHYSIOL_NETW_Vascular Resistance|PVR|PAH|ANG|ACE|TPR|AVP|MAX|F2|SI|NOS3|DBP|CAD|NPY|PC|VIP|MB|MBP|TNF|CS|CP|RHO|NOS2|LPA|RHOA|PTS|PDE5A|EPO|HP|ACTIN|NODAL|ADO|NTS|BMPR2|COPE|TH|C2|APOE|BID|NOS1|ADM|RAN|TRH|CRP|EGFR|AR|TG|MPO|DAP|PAM|C3|CAST|FGR|MPI|PIP|MARS|COIL|PTGS1|PGF|FAP|CRH|DCD|SRI|MRAP|CNP|ARC|VWF|DES|FH|TAT|CFD|PTH|AGA|SDS|GC|TRPC6|KIT|ATM|ERAS|PALM|CD59|HBD|CCL4|PGC|EMD|VEGFA|SRC|PTGS2|HMGB1|NPS|TRPC3|TANK|PPP1R12A|POLE|AES|C5|STH|PCNA|TF|TRPC4|HMOX1|CASR|CAPS|TRPV1|F3|ERG|CSK|APC|ACD|GAL|ATP1A2|ADA|REN|DPP4|ABR|DBT|CCK|SLC12A2|FEV|GHR|LPO|TYR|DAO|KY|

PHYSIOL_NETW_Vascular Stiffness|EGFR|NOS3|ANG|PVR|PAH|ACE|GLA|DBP|CAD|HP|ARG2|

Experiment 8 Example E1_Ontology for Anatomy Based Phys Sub NETW

Phy_NTW_Yawningkk_aa_kkBrain|Brain|
Phy_NTW_Yawningkk_aa_kkMouth|Mouth|
Phy_NTW_Yawningkk_aa_kkNeurons|Neurons|
Phy_NTW_Yawningkk_aa_kkHypothalamus|Hypothalamus|

Phy_NTW_Yawningkk_aa_kkNervous System|Nervous System|
Phy_NTW_Yawningkk_aa_kkHead|Head|
Phy_NTW_Yawningkk_aa_kkHeart|Heart|
Phy_NTW_Yawningkk_aa_kkEye|Eye|
Phy_NTW_Yawningkk_aa_kkTemporomandibular Joint|Temporomandibular Joint|
Phy_NTW_Yawningkk_aa_kkCentral Nervous System-|Central Nervous System|
Phy_NTW_Yawningkk_aa_kkJaw|Jaw|
Phy_NTW_Yawningkk_aa_kkTongue|Tongue|
Phy_NTW_Yawningkk_aa_kkSkin|Skin|
Phy_NTW_Yawningkk_aa_kkArm|Arm|
Phy_NTW_Yawningkk_aa_kkEustachian Tube|Eustachian Tube|
Phy_NTW_Yawningkk_aa_kkMuscles|Muscles|
Phy_NTW_Yawningkk_aa_kkNeck|Neck|
Phy_NTW_Yawningkk_aa_kkBrain Stem|Brain Stem|
Phy_NTW_Yawningkk_aa_kkEar|Ear|
Phy_NTW_Yawningkk_aa_kkFetus|Fetus|
Phy_NTW_Yawningkk_aa_kkHand|Hand|
Phy_NTW_Yawningkk_aa_kkHippocampus|Hippocampus|
Phy_NTW_Yawningkk_aa_kkDopaminergic Neurons|Dopaminergic Neurons|
Phy_NTW_Yawningkk_aa_kkFace|Face|
Phy_NTW_Yawningkk_aa_kkNucleus Accumbens|Nucleus Accumbens|
Phy_NTW_Wound Healingkk_aa_kkSkin|Skin|
Phy_NTW_Wound Healingkk_aa_kkFoot|Foot|
Phy_NTW_Wound Healingkk_aa_kkEye|Eye|
Phy_NTW_Wound Healingkk_aa_kkLeg|Leg|
Phy_NTW_Wound Healingkk_aa_kkLiver|Liver|
Phy_NTW_Wound Healingkk_aa_kkEpidermis|Epidermis|
Phy_NTW_Wound Healingkk_aa_kkLung|Lung|
Phy_NTW_Wound Healingkk_aa_kkBreast|Breast|
Phy_NTW_Wound Healingkk_aa_kkCornea|Cornea|
Phy_NTW_Wound Healingkk_aa_kkBack|Back|
Phy_NTW_Wound Healingkk_aa_kkDermis|Dermis|
Phy_NTW_Wound Healingkk_aa_kkTooth|Tooth|
Phy_NTW_Wound Healingkk_aa_kkMouth|Mouth|
Phy_NTW_Wound Healingkk_aa_kkNeck|Neck|
Phy_NTW_Wound Healingkk_aa_kkHair|Hair|
Phy_NTW_Wound Healingkk_aa_kkKidney|Kidney|
Phy_NTW_Wound Healingkk_aa_kkHeart|Heart|
Phy_NTW_Wound Healingkk_aa_kkHead|Head|
Phy_NTW_Wound Healingkk_aa_kkBlood Vessels|Blood Vessels|

Experiment 8, Example E2, Node Counts for Anatomy Based Phys Sub NETW

| network | node count |
|---|---|
| Phy_NTW__Acclimatization | 37 |
| Phy_NTW__Acid-Base Equilibrium | 15 |
| Phy_NTW__Acrosome Reaction | 32 |
| Phy_NTW__Adaptive Immunity | 37 |
| Phy_NTW__Adiposity | 96 |
| Phy_NTW__Adolescent Development | 11 |
| Phy_NTW__Adrenarche | 11 |
| Phy_NTW__Afterimage | 7 |
| Phy_NTW__Agglutination | 108 |
| Phy_NTW__Airway Remodeling | 12 |
| Phy_NTW__Airway Resistance | 69 |
| Phy_NTW__Alpha Rhythm | 15 |
| Phy_NTW__Amelogenesis | 24 |
| Phy_NTW__Anaerobic Threshold | 35 |
| Phy_NTW__Andropause | 6 |
| Phy_NTW__Anestrus | 15 |
| Phy_NTW__Anovulation | 27 |
| Phy_NTW__Antibody Affinity | 11 |
| Phy_NTW__Antibody Diversity | 3 |
| Phy_NTW__Antibody Formation | 19 |
| Phy_NTW__Antibody Specificity | 19 |
| Phy_NTW__Antigen Presentation | 77 |
| Phy_NTW__Antigen-Antibody Reactions | 3 |
| Phy_NTW__Antigenic Variation | 13 |
| Phy_NTW__Appetite Regulation | 13 |
| Phy_NTW__Arthralgia | 68 |
| Phy_NTW__Asymmetric Cell Division | 17 |
| Phy_NTW__Atrial Function | 13 |
| Phy_NTW__Atrial Pressure | 63 |
| Phy_NTW__Atrial Remodeling | 8 |
| Phy_NTW__Autoimmunity | 120 |
| Phy_NTW__Axonal Transport | 184 |
| Phy_NTW__Baroreflex | 106 |
| Phy_NTW__Beta Rhythm | 7 |
| Phy_NTW__Biological Clocks | 4 |
| Phy_NTW__Bleeding Time | 50 |
| Phy_NTW__Blinking | 40 |
| Phy_NTW__Blood Cell Count | 101 |
| Phy_NTW__Blood Circulation | 170 |
| Phy_NTW__Blood Flow Velocity | 124 |
| Phy_NTW__Blood Group Incompatibility | 7 |
| Phy_NTW__Blood Viscosity | 63 |
| Phy_NTW__Blushing | 7 |
| Phy_NTW__Body Composition | 99 |
| Phy_NTW__Body Fat Distribution | 27 |
| Phy_NTW__Body Height | 82 |
| Phy_NTW__Body Patterning | 8 |

Experiment 8, Example E3, Edge Count Descriptors for 16 Objects and 472 Physiological Subnetworks

| subnetwork node count | | | | | | | | | |
|---|---|---|---|---|---|---|---|---|---|
| 37 | 15 | 32 | 37 | 96 | 11 | 11 | 7 | 108 | |
| 12 | 69 | 15 | 24 | 35 | 6 | 15 | 27 | 11 | 3 | 19 | 19 |
| 77 | 2 | 13 | 13 | 68 | 17 | 13 | 63 | 8 | 120 | 184 | 106 |
| 7 | 4 | 50 | 40 | 101 | 170 | 124 | 7 | 215 | 7 | 99 | 27 |
| 82 | 8 | 134 | 112 | 5 | 16 | 30 | 152 | 53 | 69 | 90 | 146 |
| 9 | 10 | 40 | 21 | 36 | 2 | 60 | 206 | 15 | 55 | 9 | 35 |
| 13 | 171 | 4 | 136 | 56 | 7 | 7 | 92 | 10 | 34 | 7 | 22 |
| 49 | 74 | 3 | 14 | 17 | 126 | 40 | 5 | 12 | 15 | 7 | 2 |
| 4 | 44 | 117 | 43 | 88 | 219 | 19 | 40 | 42 | 2 | 10 | 7 |
| 57 | 56 | 27 | 82 | 162 | 30 | 3 | 19 | 68 | 69 | 20 | 33 |
| 234 | 121 | 213 | 82 | 26 | 239 | 8 | 12 | 49 | 13 | 7 | 12 |
| 4 | 59 | 5 | 103 | 115 | 6 | 3 | 117 | 61 | 32 | 10 | 11 |
| 141 | 4 | 174 | 161 | 129 | 24 | 9 | 57 | 113 | 13 | 188 | 21 |
| 15 | 70 | 77 | 9 | 76 | 45 | 5 | 12 | 7 | 33 | 5 | 4 |
| 86 | 23 | 59 | 36 | 84 | 46 | 31 | 21 | 108 | 67 | 108 | 22 |

-continued

| | | | | | | | | | | | |
|---|---|---|---|---|---|---|---|---|---|---|---|
| 3 | 176 | 118 | 8 | 13 | 58 | 32 | 19 | 6 | 104 | 167 | 257 |
| 86 | 10 | 2 | 54 | 9 | 70 | 13 | 65 | 56 | 55 | 4 | 22 |
| 50 | 28 | 8 | 2 | 70 | 78 | 79 | 11 | 2 | 167 | 113 | 4 |
| 95 | 5 | 31 | 72 | 8 | 3 | 167 | 113 | 10 | 61 | 4 | 52 |
| 4 | 225 | 148 | 105 | 8 | 33 | 80 | 21 | 28 | 40 | 36 | 42 |
| 15 | 56 | 175 | 2 | 10 | 113 | 59 | 109 | 105 | 98 | 28 | 34 |
| 231 | 211 | 201 | 47 | 78 | 105 | 147 | 15 | 4 | 57 | 51 | 13 |
| 17 | 18 | 5 | 57 | 191 | 106 | 19 | 7 | 184 | 9 | 86 | 22 |
| 44 | 31 | 80 | 8 | 136 | 6 | 19 | 52 | 54 | 26 | 18 | 135 |
| 26 | 35 | 10 | 60 | 177 | 111 | 45 | 14 | 144 | 46 | 153 | 4 |
| 5 | 114 | 100 | 8 | 73 | 125 | 13 | 16 | 20 | 39 | 12 | 144 |
| 6 | 20 | 78 | 198 | 57 | 2 | 19 | 6 | 26 | 56 | 18 | 10 |
| 27 | 14 | 40 | 71 | 66 | 3 | 173 | 106 | 42 | 37 | 19 | 50 |
| 16 | 20 | 7 | 62 | 66 | 8 | 54 | 79 | 70 | 95 | 95 | 76 |
| 21 | 16 | 184 | 63 | 7 | 3 | 23 | 36 | 19 | 65 | 21 | 117 |
| 15 | 185 | 125 | 44 | 57 | 76 | 112 | 71 | 15 | 18 | 39 | 7 |
| 136 | 27 | 53 | 52 | 24 | 111 | 23 | 7 | 10 | 5 | 5 | 31 |
| 80 | 3 | 51 | 24 | 4 | 3 | 23 | 18 | 37 | 56 | 64 | 41 |
| 56 | 42 | 8 | 16 | 32 | 112 | 31 | 70 | 27 | 82 | 31 | 16 |
| 4 | 25 | 4 | 17 | 24 | 26 | 96 | 12 | 18 | 46 | 111 | 25 |
| 68 | 165 | 212 | 24 | 75 | 187 | 79 | 201 | 4 | 10 | 53 | 39 |
| 38 | 17 | 7 | 101 | 35 | 16 | 6 | 23 | 217 | 6 | 9 | 13 |
| 98 | 11 | 106 | 31 | 23 | 4 | 56 | 7 | 19 | 209 | 207 | 153 |
| 3 | 94 | 68 | 28 | 19 | 26 | 182 | 62 | 95 | 26 | 165 | 26 |
| 65 | 22 | 124 | 257 | 23 | 263 | | | | | | | objects/subnetworks Acclimatization Acid-Base Equilibrium Acrosome Reaction Adaptive Immunity Adiposity Adolescent Development Adrenarche Afterimage Agglutination Airway Remodeling Airway Resistance Alpha Rhythm Amelogenesis Anaerobic Threshold Andropause Anestrus Anovulation Antibody Affinity Antibody Diversity Antibody Formation Antibody Specificity Antigen Presentation Antigen-Antibody Reactions Antigenic Variation Appetite Regulation Arthralgia Asymmetric Cell Division Atrial Function Atrial Pressure Atrial Remodeling Autoimmunity Axonal Transport Baroreflex Beta Rhythm Biological Clocks Bleeding Time Blinking Blood Cell Count Blood Circulation Blood Flow Velocity Blood Group Incompatibility Blood Viscosity Blushing Body Composition Body Fat Distribution Body Height Body Patterning Body Size Body Surface Area Body Temperature Regulation Body Weight Changes Bone Conduction Bone Density Bone Development Bone Regeneration Bone Remodeling Bone Resorption Brain Waves Breakthrough Pain Breast Feeding Breath Holding Breech Presentation Bronchoconstriction Capillary Permeability Capillary Resistance Cardiac Volume Cardiomegaly Cardiovascular Deconditioning Carotid Intima-Media Thickness Experiment 8, Example E4, Transformation of Edge Count Descriptors Example Oleic Acid_472 Physiological Subnetworks

| subnetwork node count | Physiology subnetwork | edge density measurements for Oleic Acid | ration of subnetwork node/edge density measurement (inverse ratio) |
|---|---|---|---|
| 37 | Acclimatization Acid-Base | 28 | 1.3 (0.75) |
| 15 | Equilibrium | 13 | 1.15 (0.86) |
| 32 | Acrosome Reaction | 15 | 2.13 (0.46) |
| 37 | Adaptive Immunity | 30 | 1.23 (0.81) |
| 96 | Adiposity | 49 | 1.95 (0.51) |
| 11 | Adolescent Development | 8 | 1.375 (0.72) |

-continued

| subnetwork node count | Physiology subnetwork | edge density measurements for Oleic Acid | ration of subnetwork node/edge density measurement (inverse ratio) |
|---|---|---|---|
| 11 | Adrenarche | 6 | 1.83 (0.54) |
| 7 | Afterimage | 6 | 1.16 (0.85) |

Experiment 9, Example F1

D_NTW_epithelial-myoepithelial carcinoma ACUTE LEUKEMIA ACUTE LYMPHOBLASTIC LEUKEMIA ADENOMA AGGRESSION ANEMIA ANOREXIA ARTHRITIS ASCITES ASPIRATION ATAXIA ATHEROSCLEROSIS ATROPHY BENIGN PROSTATIC HYPERPLASIA BLADDER CANCER BLADDER CARCINOMA BLEEDING BREAST CARCINOMA CARDIAC FAILURE CARDIOMYOPATHY CHORIOCARCINOMA CHRONIC LYMPHOCYTIC LEUKEMIA COLON CANCER CONFUSION CONGESTIVE HEART FAILURE CYST DEHYDRATION DIABETES MELLITUS DIARRHEA DYSPNEA EMESIS ENDOMETRIAL CANCER EPISTAXIS ERYTHEMA ESOPHAGEAL CARCINOMA FALL FATIGUE FEVER GASTRIC CANCER GASTRIC CARCINOMA GASTRITIS GROWTH RETARDATION HEADACHES HEPATITIS HEPATITIS B HEPATOMA HERPES SIMPLEX HYPERACTIVITY HYPERGLYCEMIA HYPERSENSITIVITY HYPERTENSION HYPERTROPHY HYPDXIA IMMUNODEFICIENCY INFLUENZA ISCHEMIA LEIOMYOMA LUNG CANCER LUNG DISEASE LYMPHOMA MELANOMA MENOPAUSE MYELODYSPLASTIC SYNDROME MYELOMA MYOCARDIAL INFARCT NAUSEA NECK STIFFNESS NEUROPATHY NEUTROPENIA NEVUS OBESITY OCCLUSION OVARIAN CANCER OVARIAN CARCINOMA PANCREATITIS PARKINSON'S DISEASE PLEURAL EFFUSION PROSTATE CANCER PROSTATE CARCINOMA RECTAL CAN- CER RELAXATION RENAL CARCINOMA RENAL CELL CANCER SARCOMA SCHIZOPHRENIA SHOCK SKIN CANCER SQUAMOUS CELL CARCINOMA STOMATITIS STROKE SWELLING SYSTEMIC LUPUS ERYTHEMATOSUS T-CELL LYMPHOMA TELANGIECTASIA THROMBOCYTOPENIA THYROID CARCINOMA WEIGHT GAIN WEIGHT LOSS WOUND D_NTW_facial hemiatrophy ATROPHY SCLERODERMA D_NTW_frozen shoulder DIABETES MELLITUS FRACTURE SHOULDER PAIN TENSION TRAUMA D_NTW_linitis plastica BREAST CARCINOMA GASTRIC CANCER GASTRIC CARCINOMA D_NTW_pleomorphic xanthoastrocytoma ACUTE LYMPHOBLASTIC LEUKEMIA ADENOMA AGGRESSION AIDS ANEMIA ARTHRITIS ASPIRATION ATAXIA ATROPHY BASAL CELL CARCINOMA BLADDER CANCER BLEEDING BREAST CARCINOMA CARDIOMYOPATHY CHRONIC LYMPHOCYTIC LEUKEMIA COLON CANCER CONFUSION CYST DERMATITIS DIABETES MELLITUS DIARRHEA EMESIS ENDOMETRIAL CANCER ENDOMETRIOSIS EPILEPSY ERYTHEMA EXCITEMENT EXTRAVASATION FALL FEVER GASTRIC CANCER GASTRIC CARCINOMA GOITER GROWTH RETARDATION HEADACHES HEPATITIS HERPES SIMPLEX HISTIOCYTOSES HYPERACTIVITY HYPERGLYCEMIA HYPERKERATOSIS HYPERSENSITIVITY HYPERTENSION HYPERTROPHY HYPOXIA IMMUNODEFICIENCY INFLAMMATORY BOWEL DISEASE ISCHEMIA KERATOSIS LUNG CANCER LUNG DISEASE LYMPHADENOPATHY LYMPHOMA MELANOMA MENTAL RETARDATION MYELODYSPLASTIC SYNDROME MYELOMA MYELOPROLIFERATIVE DISORDER NAUSEA NEUROPATHY NEUTROPENIA NEVUS OBESITY OCCLUSION OVARIAN CANCER OVARIAN CARCINOMA PANCREATITIS PARKINSON'S DISEASE PNEUMONIA PROSTATE CANCER RECTAL CANCER SARCOMA SEIZURE SHOCK SQUAMOUS CELL CARCINOMA STARVATION SWELLING TENSION THROMBOCYTOPENIA THYROID CARCINOMA ULCERATIVE COLITIS WEAKNESS WOUND D_NTW_WHIM syndrome ABUSE ACUTE LEUKEMIA ACUTE LYMPHOBLASTIC LEUKEMIA ACUTE MYELOCYTIC LEUKEMIA ADENOMA AGGRESSION AIDS ALLERGIC RHINITIS ALLERGY ANEMIA ANEURYSM ARTERIOSCLEROSIS ARTHRITIS ASCITES ASTHMA ATHEROSCLEROSIS ATROPHY BASAL CELL CARCINOMA BLADDER CANCER BLADDER CARCINOMA BLEEDING BREAST CARCINOMA BRONCHIOLITIS CARDIAC FAILURE CARDIOMYOPATHY CHORIOCARCINOMA CHRONIC LYMPHOCYTIC LEUKEMIA CHRONIC OBSTRUCTIVE PULMONARY DISEASE CMV COGNITIVE IMPAIRMENT COLON CANCER CORONARY ARTERY DISEASE CORONARY OCCLUSION CROHN'S DISEASE DEMENTIA DEMYELINATION DEPRESSION DERMATITIS DIABETES MELLITUS DIARRHEA ENCEPHALITIS ENCEPHALOPATHY ENDOMETRIAL CANCER ENDOMETRIOSIS EOSINOPHILIA ESOPHAGEAL CARCINOMA EXCITEMENT EXHAUSTION EXTRAVASATION FALL FATIGUE FATTY LIVER FEVER FRACTURE GASTRIC CANCER GASTRIC CARCINOMA GASTRIC ULCER GASTRITIS GRANULOMA GROWTH RETARDATION HEPATIC FAILURE HEPATITIS HEPATITIS B HEPATOMA HERPES SIMPLEX HYPERACTIVITY HYPERALGESIA HYPERGLYCEMIA HYPERSENSITIVITY HYPERTENSION HYPERTROPHY HYPDXIA IDIOPATHIC PULMONARY FIBROSIS IMMUNODEFICIENCY INFLAMMATORY BOWEL DISEASE INFLUENZA INTERSTITIAL PNEUMONITIS ISCHEMIA ITCH KIDNEY DYSFUNCTION LEUKOCYTOSIS LIVER CIRRHOSIS LIVER DAMAGE LIVER FAILURE LIVER NECROSIS LUNG CANCER LUNG DISEASE LUNG FIBROSIS LYMPHOCYTIC LEUKAEMIA LYMPHOMA LYMPHOPENIA MACULAR DEGENERATION MELANOMA MENOPAUSE MULTIPLE SCLEROSIS MYELODYSPLASTIC SYNDROME MYELOFIBROSIS MYELOID LEUKAEMIA MYELOMA MYOCARDIAL INFARCT NAUSEA NEPHRITIS NEPHROPATHY NERVE DAMAGE NEUROPATHY NEUROTOXICITY NEUTROPENIA OBESITY OBLITERATIVE BRONCHIOLITIS OCCLUSION OSTEOLYSIS OSTEOPOROSIS OVARIAN CANCER OVARIAN CARCINOMA PERIODONTAL DISEASE PERIODONTITIS PLEURISY PNEUMONIA POLYCYTHEMIA PROSTATE CANCER PROSTATE CARCINOMA PULMONARY FIBROSIS PULMONARY HYPERTENSION RECTAL CANCER RENAL CARCINOMA RENAL CELL CANCER RENAL DISEASE RENAL FAILURE RETINOPATHY RHINITIS SARCOMA SCARRING SCLERODERMA SEPSIS SHOCK SKIN CANCER SQUAMOUS CELL CARCINOMA STOMATITIS STROKE SUPERINFECTION SYSTEMIC LUPUS ERYTHEMATOSUS T-CELL LYMPHOMA TENSION THROMBOCYTHEMIA THROMBOCYTOPENIA THROMBOSIS THYROID CARCINOMA TIC TRAUMA TUBERCULOSIS ULCERATIVE COLITIS VAGINAL INFECTION VIRAL INFECTION VIREMIA WEIGHT LOSS WOUND D_NTW_B cell deficiency ALLERGY ANEMIA ARTHRITIS ASTHMA ATHEROSCLEROSIS ATROPHY CHRONIC LYMPHOCYTIC LEUKEMIA COLON CANCER FALL FEVER GLOMERULONEPHRITIS HEPATITIS HYPERSENSITIVITY IMMUNODEFICIENCY INFLUENZA ISCHEMIA LUNG CANCER LYMPHOMA MELANOMA MULTIPLE SCLEROSIS MYELOMA OBESITY OCCLUSION PNEUMONIA PROSTATE CANCER RENAL DISEASE SARCOMA SEPSIS SHOCK SPLENOMEGALY SWELLING SYSTEMIC LUPUS ERYTHEMATOSUS THROMBOCYTOPENIA TUBERCULOSIS WOUND

The invention claimed is:

1. A method of tracking information flows through multiple network systems comprising:
   selecting a primary network system from a population of primary and secondary network systems, wherein each of the primary and secondary network systems comprise network nodes;
   selecting first selected characteristic features that identify network nodes of the primary network system that provide interaction between the selected primary network system and secondary network systems;

identifying at least one secondary network system that is capable of interacting with the network nodes of the primary network system;

subdividing the primary network into subnetwork systems based on identifying primary network nodes that provide interaction between the primary network system and secondary network nodes;

identifying the subnetwork systems that are capable of interacting with one or more network nodes of the secondary network systems;

identifying a subnetwork node count of the primary network nodes in each subnetwork;

identifying objects that are capable of interacting with the primary network nodes; and determining a coincidence frequency or a coincidence measurement between features of objects interacting with the primary network nodes and the features of the primary network nodes that indicate information exchanges between the primary and secondary network nodes.

2. The method of claim 1, wherein the first selected characteristic features are selected from proper names, synonyms or symbols of network nodes of interaction network systems, measurements associated with network nodes of interaction network systems, a plurality of measurements associated with network nodes of interaction network systems, proper names and synonyms of groups of network nodes of interaction networks, symbols of network nodes of interaction network systems, and symbols of groups of network nodes of interaction network systems.

3. The method of claim 1, wherein identifying at least one secondary network system that is capable of interacting with the network nodes of the primary network system includes:

randomly selecting second selected characteristic features of network nodes of randomly selected interaction networks stored in a database;

using the first selected characteristic features and the second selected characteristic features for determining coincidence frequencies or coincident measurements of the first selected characteristic features with the second selected characteristic features and recording the results; and using the recorded coincidence frequency or coincidence measurement results for selecting one or more secondary network systems having at least one network node capable of interacting with the primary network system.

4. The method of claim 3, wherein the database comprises one or more of the Medline database, PubMed databases, EMBL databases, World Traditional Medicine Patent Database, Chinese Traditional Medicine Database, complementary and alternative medicine databases, Wikipedia, collections of digitized publications, measurements collected by surveillance systems, measurements collected by bio-surveillance systems, measurements collected by diagnostic systems, measurements collected by wearable devices, measurements collected by wearable electronic systems, measurements collected by wearable sensors, measurements collected by wearable diagnostic systems, measurements collected through crowd sourcing, medical record databases, adverse event reporting system databases, DHARA databases, and Ayurveda health care system databases.

5. The method of claim 1, wherein the secondary network systems comprise one or more of the internet, social networks, ecologic networks, biologic networks, nutrient networks, biologic communication networks, epidemiologic networks, protein networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks, military networks, immunologic networks, and intelligence networks.

6. The method of claim 1, wherein subdividing the primary network into subnetworks includes:

selecting characteristic features of the primary network nodes;

selecting characteristic features of the secondary network nodes; and using the characteristic features of the primary network nodes and secondary network nodes for determining coincident measurements or co-occurrence frequency measurements indicating interactions between the primary network nodes and secondary network nodes in the database and recording the results.

7. The method of claim 1, comprising determining the capacity of the objects to affect information transfer between the primary network system and a selected secondary network system using:

a first process including:
selecting ontologies of the subnetworks; and
selecting ontologies of objects capable of interacting with said subnetwork for determining coincidence frequencies or coincidence measurements between instances in said subnetworks ontologies and instances in said object ontologies; and
recording the result for said co-occurrence frequency or coincidence measurements;

a second process including:
selecting a threshold for said co-occurrence frequency or coincidence measurements for determining the number of subnetwork nodes in subnetworks having co-occurrence frequencies or coincidence measurements above said selected threshold; and
recording the results as object reachable subnetwork node counts of the subnetworks or as edge density measurements for said object and said subnetworks; and
storing the results as edge density based object descriptors that provide estimates for the capacity of the objects to affect a transfer of information between the primary network system and a selected plurality of the secondary network systems.

8. The method of claim 7, further comprising normalizing the edge density based object descriptors by determining ratios of the edge density measurements and the subnetwork node counts of the subnetworks of the primary network system.

9. The method of claim 8, wherein the ratios are determined using an instance of object associated edge density measurements as a numerator and an instance of subnetwork node counts of subnetworks of the primary network as a denominator, and the method includes recording the resulting node count ratios.

10. The method of claim 8, wherein the ratios are determined using an instance of object associated edge density measurements as a denominator and an instance of subnetwork node counts of subnetworks of the primary network as a numerator, and the method includes recording the resulting node count ratios.

11. The method of claim 8, comprising aggregating the count ratios for the selected subnetworks and using the aggregated count ratios as estimates of the capacity of objects to affect information transfer between selected subnetworks of the selected primary network system and a selected secondary network system.

12. The method of claim 7, comprising using the edge density based object descriptors for information flow analysis.

13. The method of claim 7, wherein the subnetwork ontologies are derived from protein networks for creating the descriptors for information flow analysis.

14. The methods of claim 7, wherein the sub network ontologies are disease based and derived from protein networks for creating the descriptors for information flow analysis.

15. The methods of claim 7, wherein the sub network ontologies are Medra Term based sub network ontologies derived from protein networks for creating the descriptors for information flow analysis.

16. The methods of claim 7, wherein the sub network ontologies are physiology based sub network ontologies derived from protein networks for creating the descriptors for information flow analysis.

17. The method of claim 7, comprising using the edge density based object descriptors for information flow analysis for selected herbs and drugs using disease based sub network ontologies derived from protein networks.

18. The method of claim 7, comprising using the edge density based object descriptors for information flow analysis for selected herbs and drugs using Medra Term based sub network ontologies derived from protein networks.

19. The method of claim 7, comprising using the edge density based object descriptors for information flow analysis for selected herbs and drugs using physiology based sub network ontologies derived from protein networks.

20. The method of claim 1, comprising determining a second set of descriptor sets by:
　identifying objects that are capable of interacting with the primary network nodes by selecting characteristic features of the objects and determining occurrence frequencies or coincident measurements between the selected characteristic features of the objects and characteristic features of the primary network nodes;
　identifying and counting a number of network nodes in each subnetwork of the primary network that are capable of interacting or exchanging information with the identified objects;
　recording the node counts as focused subnetwork node counts;
　adding the co-occurrence frequency or coincident measurements of objects associated with respective subnetwork nodes of subnetworks of the primary network and recording the results as identifying a sum of co-occurrence frequency measurements for the objects obtained for each subnetwork node of subnetworks of the primary network 200;
　storing the sum of co-occurrence frequency measurements of said objects for said subnetwork node of the primary network as information density measurements of the objects, wherein the information density measurements of said objects provide estimates of the capacity of objects to affect information transfer between the subnetworks and the selected secondary network systems;
　further comprising aggregating the information density measurements of said objects for the selected subnetworks and using the aggregated information density measurements of said objects as estimates of the capacity of objects to affect information transfer between selected subnetworks of the selected primary network system and a selected secondary network system.

21. The method of claim 20, comprising using the second descriptor set for information flow analysis.

22. The method of claim 20, comprising using the second descriptor set for information flow analysis for selected herbs and drugs using disease based sub network ontologies derived from protein networks.

23. The method of claim 20, comprising using the second descriptor set for information flow analysis for selected herbs and drugs using Medra Term based sub network ontologies derived from protein networks.

24. The method of claim 20, comprising using the second descriptor set for information flow analysis for selected herbs and drugs using physiology based sub network ontologies derived from protein networks.

25. The method of claim 1, comprising using the second descriptor set in hierarchical cluster analysis to identify groups of objects that induce similar routing of information flows in a plurality of interacting network systems and groups of network topologies regulating similar information flows.

26. A method for producing novel descriptors of objects or persons comprising:
　a first step of selecting a first set of characteristic features of network-nodes of a first interaction network system of interest further comprising the use of said selected characteristic features of said network nodes of said first selected interaction network system for creating a first descriptor set of said first interaction network system;
　wherein the characteristic features may be selected from the group comprising proper names, synonyms or symbols of network nodes of interaction network systems, measurements associated with network nodes of interaction network systems, a plurality of measurements associated with network nodes of interaction network systems, proper names and synonyms of groups of network nodes of interaction networks, symbols of network nodes of interaction network systems, symbols of groups of network nodes of interaction network systems;
　wherein the interaction network systems may be selected from the group comprising the internet, social networks, ecologic networks, biologic networks, epidemiologic networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks;
　a second step of using said first descriptor set of said first network system for selecting a second, third, fourth . .

. nth interaction network system interacting directly or indirectly or exchanging information directly or indirectly with said first interaction network system by using:
- a first process for randomly selecting characteristic features of network-nodes of randomly selected interaction networks in a databases;
- a second process using said first descriptor set of said first network system and said randomly selected characteristic features of network nodes of said randomly selected interaction network system for determining coincidence frequencies or coincident measurements of said first descriptor set with said randomly selected characteristic features of network nodes of said randomly selected interaction networks in said database and recording the results; and
- a third process using said recorded results for selecting a second, third, fourth . . . nth interaction network system possessing at least one network node capable of interacting with or exchanging information with said first selected interaction network system;

wherein the database may be selected from the group comprising the Medline database, PubMed databases, EMBL databases, World Traditional Medicine Patent Database, Chinese Traditional Medicine Database, complementary and alternative medicine database, Wikipedia, collections of digitized publications, measurements collected by surveillance systems, measurements collected by bio surveillance systems, measurements collected by diagnostic systems, measurements collected by wearable devices, measurements collected by wearable electronic systems, measurements collected by wearable sensors, measurements collected by wearable diagnostic systems, measurements collected through crowd sourcing, medical record database, adverse event reporting system database, DHARA database, Ayurveda health care system databases;

wherein the second process for determining coincidence frequencies or coincident measurements comprises the selection of an instance of a first descriptor set and the selection of an instance of a second descriptor set and the selection of a database and the use of a text mining means for determining how often an instance of a first descriptor set co-occurs with an instance of a second descriptor set in said database and recording the results; likewise determination of coincidence measurements comprises the selection of an instance of a first descriptor set and the selection of an instance of a second descriptor set and the selection of a data bases and the use of a means for identifying measurements relating an instance of a first descriptor set and an instance of a second descriptor set in said database and recording the results;

a third step comprising a third method for selecting a second, third, fourth . . . nth set of characteristic features of network-nodes of said second, third, fourth, nth interaction network system further comprising the use of said second, third, fourth . . . nth set of characteristic features of said network nodes of said second, third, fourth, . . . nth interaction network system for creating a second, third, fourth . . . nth descriptor set of said second, third, fourth . . . nth interaction network system selected in said second step;

a fourth step comprising a fourth method using said first descriptor set of said first interaction network system and using said second, third, fourth . . . nth descriptor set of said second, third, fourth . . . nth interaction network system and said second process of said second step and said databases for selecting subsets of descriptor sets of said first interaction network systems describing subsets of network nodes of said first interaction network system interacting directly or indirectly or exchanging information directly or indirectly with network nodes of said second, third, fourth . . . nth interaction network system;

a fourth process for determining the number of network nodes in said first, second, third, fourth subnetwork system of said first interaction network systems and recording the results wherein said results may be termed first, second, third, fourth . . . nth subnetwork-node counts of said subnetwork system of said first interaction network system are further termed SN1-nCN1 a fifth step comprising a fifth method for selecting a finite set of objects termed O1-m interacting directly or indirectly or exchanging information directly or indirectly with said first interaction network system, wherein said fifth method comprises a fifth process using said first descriptor set of said first interaction network system and using randomly selected characteristic features of randomly selected objects and said second process of said second step and said databases for determining coincidence frequencies or coincident measurements of said first descriptor set with said randomly selected characteristic features of said randomly selected objects in said databases;

selecting coincidence frequency measurements or a coincident measurement threshold and using said threshold for selecting incidences of said coincidence frequency measurements or said coincident measurements for said descriptor sets in said databases and recording the results;

using said selected coincidence frequency measurements or coincident measurements for selecting objects capable of interacting or exchanging information with at least one or a plurality of network nodes of said first selected interaction network system and recording said selected objects in a database;

wherein the objects are selected from the group comprising members of social networks, members of financial networks, members of ecologic networks, prescription medicines, over the counter drugs, medicinal herbs, natural products, Ayurvedic medicines, Chinese traditional medicines, Natural medicines, bacteria, algae, Organic and inorganic chemical compositions, Foods, nutrients, vitamins, microorganisms, viruses, supplements, vitamins, mobile devices, patients, clients, communities, members of communities, financial instruments, bonds, companies, members of physiologic networks, members of organ system networks, members of cellular networks members of tissue networks a sixth step comprising the selection of a first set of characteristic features of said selected objects and the use of said characteristic features of said selected objects as first intermittent descriptor set of said selected objects;

wherein the first set of characteristic features of said objects are selected from the group comprising proper names and synonyms of objects, symbols for objects, collection of physical properties of objects, collections of measurements associated with objects, unique identifiers of objects in a database a seventh step comprising a sixth method using said first intermittent descriptor set of said objects and using said first, second, third, fourth . . . nth subnetwork descriptor sets of said first selected interaction network system and using said second process of said second step and using said databases for identifying objects capable of interacting directly or indirectly or of exchanging information directly or indirectly with at least one network node of said first, second, third, fourth . . . nth subnetwork system of said first network system and recording the results;

the sixth method may comprise a process using said first set of intermittent object descriptors and said first, second, third, fourth . . . nth set of subnetwork descriptors of said first, second, third, fourth . . . nth subnetwork of said first selected interaction network system and said second process of said second step and said databases for determining coincidence frequencies or coincident measurements of said first set of intermittent object descriptors and said first, second, third, fourth . . . nth subnetwork descriptors of said subnetwork systems of said first selected interaction network system in said database and recording the results;

selecting a threshold of said coincidence frequency measurements or coincident measurements for selecting at least one or a plurality of network nodes in said first, second, third, fourth . . . nth subnetwork system of said first interaction network system capable of interacting or exchanging information with said objects;

a tenth process for counting the number of said selected network nodes for said subnetwork systems and said objects and recording the results wherein said results are termed first, second, third, fourth . . . nth object-subnetwork-interaction node counts hereinafter further termed O1-n SN1-n ICN1;

an eight step including a seventh method using said object-subnetwork-interaction node counts termed O1-n SN1-n ICN1 of said objects as numerators and using said subnetwork-node counts termed SN1-nCN1 of said subnetworks of said first interaction network system as denominator for determining the ratio between said subnetwork node counts and recording the result for said objects O1-m and said subnetwork system SN11-n wherein said results, termed normalized first, second, third, fourth object subnetwork-interaction interference scores, are further termed O1-mSN1-n IFSCN1;

a ninth step comprising the recording of said normalized object-subnetwork interaction interference scores O1-mSN1-n IFSCN1 for said subnetwork systems as descriptors of said objects in a database;

a tenth step comprising an eighth method using said object-subnetwork interaction interference scores O1-mSN1-n IFSCN1 and an eleventh process for determining similarities between said object-subnetwork interaction interference scores of said objects and displaying the results;

wherein the eleventh process is selected from the group comprising hierarchical cluster analysis, principal component analysis, vector machines, k means analysis, profile similarity analysis.

27. The method of claim 26, wherein the objects are selected from the group comprising members of social networks, members of financial networks, members of ecologic networks, prescription medicines, over the counter drugs, medicinal herbs, natural products, Ayurvedic medicines, Chinese traditional medicines, Natural medicines, bacteria, algae, Organic and inorganic chemical compositions, Foods, nutrients, vitamins, microorganisms, viruses, supplements, vitamins, mobile devices, patients, clients, communities, members of communities, financial instruments, bonds, companies, members of physiologic networks, members of organ system networks, members of cellular networks members of tissue networks.

28. The method of claim 26, wherein the descriptors are used for determining similarities between information flows induced by said objects or persons in interaction networks, and wherein said interaction networks are selected from the group comprising the internet, social networks, ecologic networks, biologic networks, epidemiologic networks, supply networks, demand networks, shopping networks, electricity networks, power transmission networks, manufacturing networks, traffic networks, communication networks, wireless networks, financial networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks, health care networks, security networks, criminal networks.

29. The method of claim 26, wherein the network systems are selected from the group comprising epidemiologic networks, biologic communication networks, protein networks, cellular networks, cellular pathways, metabolic networks, gene networks, physiologic networks, organ system networks, cellular communication networks, cell signaling networks, intracellular communication networks, neuronal networks, disease networks, organelle networks, bacterial networks, viral networks.

30. The method of claim 26, wherein the objects are selected from the group comprising prescription medicines, traditional medicines, medicinal herbs, foods, natural products, experimental medicines, Ayurvedic medicines, microorganisms, infectious agents.

31. The method of claim 26, wherein the coincidence measurements are selected from the group comprising measurements produced by wearable devices.

* * * * *